United States Patent
Zhang et al.

(10) Patent No.: US 10,571,368 B2
(45) Date of Patent: Feb. 25, 2020

(54) AUTOMATED SYSTEM AND METHOD FOR ADVANCING TAPE TO TRANSPORT CUT TISSUE SECTIONS

(71) Applicant: Clarapath, Inc., New York, NY (US)

(72) Inventors: Cong Zhang, Burlington, MA (US); Mark Fasciano, Port Washington, NY (US); Partha P. Mitra, New York, NY (US)

(73) Assignee: Clarapath, Inc., New York, NY (US)

( * ) Notice: Subject to any disclaimer, the term of this patent is extended or adjusted under 35 U.S.C. 154(b) by 71 days.

(21) Appl. No.: 15/476,983

(22) Filed: Apr. 1, 2017

(65) Prior Publication Data

US 2017/0205317 A1 Jul. 20, 2017

Related U.S. Application Data

(63) Continuation-in-part of application No. 15/179,916, filed on Jun. 10, 2016.

(60) Provisional application No. 62/325,519, filed on Apr. 21, 2016, provisional application No. 62/320,114, filed on Apr. 8, 2016, provisional application No. 62/187,114, filed on Jun. 30, 2015.

(51) Int. Cl.
*G01N 1/06* (2006.01)
*G01N 1/31* (2006.01)
*G01N 35/00* (2006.01)

(52) U.S. Cl.
CPC ............... *G01N 1/06* (2013.01); *G01N 1/31* (2013.01); *G01N 1/312* (2013.01); *G01N 35/00009* (2013.01); *G01N 2001/061* (2013.01); *G01N 2035/00019* (2013.01)

(58) Field of Classification Search
CPC ............ G01N 1/06; G01N 1/31; G01N 1/312; G01N 2001/061; B26F 1/38
See application file for complete search history.

(56) References Cited

U.S. PATENT DOCUMENTS

| | | |
|---|---|---|
| 3,552,247 A | 1/1971 | Pickett |
| 3,667,330 A | 6/1972 | Kobernick |
| 3,690,933 A | 9/1972 | Cole |
| 3,690,988 A | 9/1972 | Ullberg et al. |
| 3,832,923 A | 9/1974 | Lassmann et al. |
| 3,939,019 A | 2/1976 | Pickett |

(Continued)

FOREIGN PATENT DOCUMENTS

| | | |
|---|---|---|
| JP | 2008/216109 | 9/2008 |
| WO | WO 2012/033842 | 3/2012 |

OTHER PUBLICATIONS

PCT/US2017/025638 Partial International Search Report dated Aug. 1, 2017.

(Continued)

*Primary Examiner* — Benjamin R Whatley
(74) *Attorney, Agent, or Firm* — Neil D. Gershon

(57) ABSTRACT

An automated tape transfer apparatus including a tape feed mechanism feeding a continuous length of an adhesive tape through the automated tape transfer apparatus and a tape applicator applying the adhesive tape to a cutting face of a sample block, wherein a section of the sample block is adhered to the adhesive tape after cutting of the section from the sample block. A slide station transfers the cut section from the adhesive tape to a slide.

18 Claims, 20 Drawing Sheets

(56) References Cited

U.S. PATENT DOCUMENTS

| | | | |
|---|---|---|---|
| 4,190,472 | A * | 2/1980 | Slonicki ............... G01N 1/312 156/357 |
| 4,257,346 | A | 3/1981 | Ornstein et al. |
| 4,264,560 | A | 4/1981 | Natelson |
| 4,545,831 | A | 10/1985 | Ornstein |
| 4,752,347 | A | 6/1988 | Rada |
| 4,883,642 | A | 11/1989 | Bisconte |
| 5,156,019 | A | 10/1992 | McCormick |
| 5,444,105 | A | 8/1995 | Ornstein |
| 5,480,508 | A | 1/1996 | Manabe et al. |
| 5,713,255 | A | 2/1998 | Izvozichikov et al. |
| 5,740,708 | A | 4/1998 | Tabone |
| 5,746,855 | A | 5/1998 | Bolles |
| 5,958,341 | A | 9/1999 | Chu |
| 6,253,653 | B1 | 7/2001 | Walter et al. |
| 6,330,348 | B1 | 12/2001 | Kerschmann et al. |
| 6,387,653 | B1 | 5/2002 | Voneiff et al. |
| 6,568,307 | B1 | 5/2003 | Gunther et al. |
| 6,598,507 | B1 | 7/2003 | Gunther et al. |
| 6,634,268 | B1 | 10/2003 | Guenther et al. |
| 6,715,870 | B2 | 4/2004 | Kiene et al. |
| 6,720,191 | B1 | 4/2004 | Goldstein |
| 7,374,907 | B1 | 5/2008 | Voneiff et al. |
| 7,503,245 | B2 | 3/2009 | Miyazawa et al. |
| 7,677,289 | B2 | 3/2010 | Hayworth et al. |
| 7,811,518 | B2 | 10/2010 | Kokubo |
| 7,866,464 | B2 | 1/2011 | Miyatani et al. |
| 7,966,091 | B2 | 6/2011 | Fujimoto et al. |
| 8,048,206 | B2 | 11/2011 | Schmitt et al. |
| 8,051,760 | B2 | 11/2011 | Walter |
| 8,056,456 | B2 | 11/2011 | Walter |
| 8,074,547 | B2 | 12/2011 | Ito et al. |
| 8,192,136 | B2 | 6/2012 | Walter et al. |
| 8,256,332 | B2 | 9/2012 | Walter |
| 8,272,225 | B2 | 9/2012 | Walter |
| 8,640,585 | B2 | 2/2014 | Zust et al. |
| 8,647,836 | B2 | 2/2014 | Heid et al. |
| 8,687,858 | B2 | 4/2014 | Walter et al. |
| 8,869,666 | B2 | 10/2014 | Yang et al. |
| 8,967,024 | B2 | 3/2015 | Magavi et al. |
| 8,996,570 | B2 | 3/2015 | Stratman et al. |
| 9,032,854 | B2 | 5/2015 | Yang et al. |
| 9,057,671 | B1 | 6/2015 | Orfield et al. |
| 9,250,253 | B2 | 2/2016 | Markin |
| 9,304,064 | B2 | 4/2016 | Walter |
| 9,541,473 | B2 | 1/2017 | Walter |
| 9,915,816 | B2 | 3/2018 | Alessi |
| 10,012,567 | B2 | 7/2018 | Bui et al. |
| 10,087,016 | B2 | 10/2018 | Nakajima et al. |
| 10,139,613 | B2 | 11/2018 | Hing et al. |
| 2002/0188224 | A1 | 12/2002 | Roe |
| 2005/0126311 | A1 | 6/2005 | Miyazawa |
| 2005/0235542 | A1 | 10/2005 | Metzner et al. |
| 2006/0008790 | A1 | 1/2006 | Hayworth et al. |
| 2007/0039435 | A1 | 2/2007 | Kokubo |
| 2007/0157786 | A1 | 7/2007 | Miyatani et al. |
| 2007/0180965 | A1 | 8/2007 | Ito et al. |
| 2007/0199418 | A1 | 8/2007 | Ito |
| 2007/0204734 | A1 | 9/2007 | Ito et al. |
| 2007/0204740 | A1 | 9/2007 | Miyatani et al. |
| 2008/0072723 | A1 | 3/2008 | Nakajima et al. |
| 2008/0088834 | A1 | 4/2008 | Miyatani et al. |
| 2008/0202308 | A1 | 8/2008 | Fujiwara et al. |
| 2009/0133556 | A1 | 5/2009 | Ito et al. |
| 2009/0137028 | A1 | 5/2009 | Ito et al. |
| 2009/0181422 | A1 | 7/2009 | Schmitt et al. |
| 2009/0241751 | A1 | 10/2009 | Walter |
| 2010/0030364 | A1 | 2/2010 | Fujimoto et al. |
| 2010/0047860 | A1 | 2/2010 | Fukuoka et al. |
| 2010/0050839 | A1 | 3/2010 | Miyatani et al. |
| 2010/0058913 | A1 | 3/2010 | Walter |
| 2010/0089516 | A1 | 4/2010 | Kawamoto |
| 2010/0093022 | A1 | 4/2010 | Hayworth et al. |
| 2010/0101385 | A1 | 4/2010 | Walter et al. |
| 2010/0118133 | A1 | 5/2010 | Walter et al. |
| 2010/0216221 | A1 | 8/2010 | Walter et al. |
| 2010/0229702 | A1 | 9/2010 | Fujimoto et al. |
| 2010/0279342 | A1 | 11/2010 | Kijima et al. |
| 2011/0303352 | A1 | 12/2011 | Nakajima et al. |
| 2012/0011975 | A1 | 1/2012 | Ito et al. |
| 2013/0166072 | A1 | 6/2013 | Yang et al. |
| 2014/0026683 | A1 | 1/2014 | Hayworth et al. |
| 2014/0041500 | A1 | 2/2014 | Isagawa et al. |
| 2014/0137715 | A1 | 5/2014 | Sneyders et al. |
| 2015/0008096 | A1 | 1/2015 | Ito |
| 2015/0017679 | A1 | 1/2015 | Ito |
| 2015/0260619 | A1 | 9/2015 | Ott et al. |
| 2015/0323925 | A1 | 11/2015 | Kondo |
| 2016/0084741 | A1 | 3/2016 | Bambot et al. |
| 2016/0245728 | A1 | 8/2016 | Walter et al. |
| 2016/0290895 | A1 | 10/2016 | Daniel et al. |
| 2017/0284904 | A1 | 10/2017 | Lim et al. |
| 2017/0363519 | A1 | 12/2017 | Gong et al. |

OTHER PUBLICATIONS

Palmgren, Axel. "Tape for Microsectioning of Very Large, Hard or Brittle Specimens." Nature 174.4418 (1954): 46. Web.

Woo, J. Y. Techniques for Sectioning and Staining Tissue Cultures of Western White Pine. Ogden, UT: U.S. Dept. of Agriculture, Forest Service, Intermountain Forest & Range Experiment Station, 1970. Print.

* cited by examiner

AUTOMATED SYSTEM AND METHOD FOR ADVANCING TAPE TO TRANSPORT CUT TISSUE SECTIONS

This application claims priority from provisional application Ser. No. 62/320,114, filed Apr. 8, 2016 and from provisional application Ser. No. 62/325,519 filed Apr. 21, 2016, and is a continuation in part of application Ser. No. 15/179,916, filed Jun. 10, 2016, which claims priority from provisional application Ser. No. 62/187,114, filed Jun. 30, 2015. The entire contents of each of these applications are incorporated herein by reference.

BACKGROUND

Field

The present invention relates to an automated system and method for advancing a tape to transport cut tissue sections from a microtome and for transferring the cut tissue sections to slides.

Description of Related Art

Traditional microtomy, the production of postage-stamp sized, micron-thin tissue sections for microscope viewing, is a delicate, time consuming manual task. In the process, a microtome cuts a tissue block consisting of tissue sample, enclosed in a supporting block of embedding material such as paraffin wax. The microtome holds a blade aligned for cutting slices from one face of tissue block—the block cutting face. A common type, the rotary microtome, linearly oscillates a chuck holding the block with the cutting face in the blade-cutting plane. Combined with incremental advancement of the block cutting face into the cutting plane, the microtome successively shaves thin tissue sections off the block cutting face. For sections with paraffin wax embedding medium, an operator carefully picks up these tissue sections and floats them on warm water. The water gently de-wrinkles and reduces deformation from cutting. Finally, an operator moves the sections from water onto microscope slides for further processing.

In addition, recent advancements in the digital imaging of tissue sample sections have made it desirable to slice blocks of specimen very quickly. By way of example, where tissues are sectioned as part of clinical care, time is an important variable in improving patient care. Every minute that can be saved during sectioning of tissue for intra-operative applications of anatomic pathology, for example in examining margins of lung cancers to determine whether enough tissue has been removed, is of clinical value. To create a large number of sample sections quickly, it is desirable to automate the process of cutting tissue sections from a specimen block by a microtome blade and facilitating the transfer of cut tissue sections to an adhesive tape without reducing section quality.

Additionally, the large number of tissue sample sections cut from the block need to be transferred to slides for evaluation. As can be appreciated, if the process of cutting the samples is automated, but the transfer to slides is performed manually, then not all of the advantages of automation are achieved.

Therefore it would be advantageous to automate one or more of these transfer functions. That is, in addition to an automated system of transferring the cut tissue sections to a continuously fed tape, an automated system that also transfers tissue sections to slides would even further enhance sample integrity and improve consistency. Additionally, such automation could decrease the need for dedicated technician time and less training time for technicians, therefore reducing costs and allowing a greater number of samples to be transferred to the slides than if performed manually.

SUMMARY

The present invention provides an automated system and method for cutting tissue sample sections from a sample block, transferring the cut tissue sample sections to tape and transferring the sections to slides.

In accordance with one aspect of the present invention, an automated tape transfer (advancement) apparatus is provided having a feed mechanism that feeds a continuous length of an adhesive tape through the automated tape transfer apparatus, a tape applicator that applies the adhesive tape to a cutting face of a sample block, wherein the adhesive tape supports the cutting face for cutting a section of the sample block and wherein the section is adhered to the adhesive tape after the cutting and a slide station that transfers the section from the adhesive tape to a slide.

In accordance with another aspect of the present invention, an automated tape transfer (tape advancement) apparatus is provided, comprising a tape feed mechanism that feeds a continuous length of an adhesive tape through the automated tape transfer apparatus, a tape applicator that applies the adhesive tape to a cutting face of a sample block, wherein a section of the sample block is adhered to the adhesive tape after cutting, the section from the sample block and a slide station that transfers the section from the adhesive tape to a slide.

In some embodiments, the adhesive tape covers the entire cutting face during cutting the section of the sample block.

In some embodiments, the tape applicator includes a roller member coupled to a linear actuator member, wherein an extension of the linear actuator member causes the roller member of the tape applicator to apply the adhesive tape to the cutting face. In some embodiments, the tape applicator further includes a spring member that causes the roller member to apply a force to the cutting face that is normal when the linear actuator member is extended.

The apparatus can include in some embodiments, a take-up mechanism that takes up the adhesive tape after the adhesive tape has exited the slide station.

In some embodiments the feed mechanism includes a controllable motor that controls properties of the feeding of the adhesive tape through the automated tape transfer apparatus. The properties can include for example one or more of a speed of the feed through the automated tape transfer apparatus, an acceleration of the feed, a jerk of the feed, and a slack of the adhesive tape within the automated tape transfer apparatus.

In some embodiments, the apparatus further includes a controller that controls the motor, wherein the controller receives inputs from sensors that are included in the automated tape transfer apparatus.

In some embodiments, the section is cut by a microtome and the automated tape transfer apparatus is coupled to the microtome.

In some embodiments, the paraffin block face could be cooled down and humidified. Cooling down the paraffin block helps increase the hardness of the medium Harder paraffin blocks can be cut at a given thickness more consistently. Humidification of the tissue and the paraffin blocks helps to avoid tissue crumbling.

In some embodiments, a heating mechanism is provided to heat one of a blade of the microtome, the sample block or the adhesive tape, wherein the heating causes an embedding medium of the sample block to enter a plastic state prior to the blade of the microtome cutting the section.

In some embodiments, the apparatus sends a signal to the microtome when the section is ready to be cut.

In some embodiments, a strength of an adhesive material of the adhesive tape is decreased after the transfer of the section to the slide by one or more of heating the adhesive material, cooling the adhesive material or exposing the adhesive material to an ultra-violet (UV) light source.

In accordance with another aspect of the present invention a method is provided comprising a) applying a first portion of a continuous length of an adhesive tape to a first cutting face of a sample block; b) moving the first portion of the adhesive tape away from the sample block after a first section has been cut from the sample block, wherein the first section is adhered to the first portion of the adhesive tape and the cutting exposes a second cutting face of the sample block; c) applying a second portion of the continuous length of the adhesive tape to the second cutting face of the sample block; d) moving the second portion of the adhesive tape away from the sample block after a second section has been cut from the sample block, wherein the second section is adhered to the second portion of the adhesive tape; e) moving the first and second portions of the continuous length of the adhesive tape that include the corresponding first and second sections to a slide station; and f) transferring the first section to a first slide.

In some embodiments, the method further comprises transferring the second section to a second slide.

In some embodiments a distance between the first portion and second portion of the adhesive tape is controlled. In some embodiments one or more of a speed, acceleration and jerk of each of the moving operations is controlled.

In some embodiments, the adhesive tape has properties that provide a support structure for the cutting face when the section is cut.

In some embodiments, the applying operations include pressing a roller member that holds the adhesive tape in a direction that is normal to the cutting face throughout an entire length of the cutting face. In some embodiments, the applying operations include melting a hot melt adhesive layer of the adhesive tape and cooling the hot melt adhesive layer to adhere the adhesive tape to the first and second cutting faces of the sample block.

In some embodiments, the method further comprises melting the hot melt adhesive layer in the first and second portions of the adhesive tape after the first and second section have been cut and prior to transferring the first and second sections to the corresponding slide or alternatively during transferring the first and second sections to the corresponding slide.

In accordance with another aspect of the present invention, an automated tape transfer apparatus is provided comprising a tape feed mechanism feeding a continuous length of an adhesive tape through the automated tape transfer apparatus and a tape applicator applying the adhesive tape to a cutting face of a sample block, wherein the tape applicator is movable from a first retracted position to a second position to move the adhesive tape into contact with the cutting face and apply a pressure against the tape and sample block to adhere the adhesive tape to the cutting face.

In some embodiments, the tape applicator includes a roller engageable with the tape and movable along the adhesive tape along a length of the cutting face. In some embodiments, the tape applicator is movable initially in a linear direction toward the sample block and subsequently in a direction along the sample block.

In accordance with another aspect of the present invention, a tape applicator apparatus is provided comprising a roller member or a cam that is in contact with an adhesive tape; and a linear actuator member coupled to the roller member, wherein the linear actuator member extends a first distance in a first direction causing the roller member to contact a cutting face of a sample block, wherein the roller member applies the adhesive tape to the cutting face.

In some embodiments, the linear actuator member extends a second distance in the first direction causing the linear actuator member to rotate about a first axis, wherein as the linear actuator member rotates about the first axis, the roller member moves to apply the adhesive tape to an entire length of the cutting face and wherein the linear actuator member retracts causing the roller member to lose contact with the cutting face.

In accordance with another aspect of the present invention, an automated tape transfer system is provided comprising a) a feed mechanism that feeds a continuous length of tape through the automated tape transfer system, the tape having an adhesive portion; b) a tape applicator that applies the adhesive portion of the tape to a sample block; c) a cutting mechanism to cut a section from the sample block for transfer to the adhesive portion; and d) a slide station that transfers the cut section of the sample from the adhesive portion to a slide.

In some embodiments, the adhesive portion is separated from the tape prior to transport to the slide station. In other embodiments, the adhesive portion extends continuously along the tape.

The system can include in some embodiments, a plurality of spaced apart adhesive portions along the tape.

The system in some embodiments can include a guide movable from a first position to a second position to change the angle of the tape relative to the sample.

In accordance with another apsect of the present invention, an automated apparatus for transferring cut sections from a sample block to slides is provided comprising a feed mechanism, A continuous tape fed by the feed mechanism, the continuous tape having a plurality of regions (or sections), each region carrying a cut section from the sample block, a slide station supporting a plurality of slides, wherein the continuous tape is movable to the slide station wherein the cut sections are aligned with slides and a movable transferring portion movable from a first position to a second position to move the continuous tape and cut sections into engagement with the slides for transfer of the cut sections to the slides.

In some embodiments, a conveyor belt is provided for transferring slides to the slide station. In some embodiments, the transferring portion includes a roller or alternatively a cam. In some embodiments, the slide station includes a UV source.

DETAILED DESCRIPTION

Figure 1:
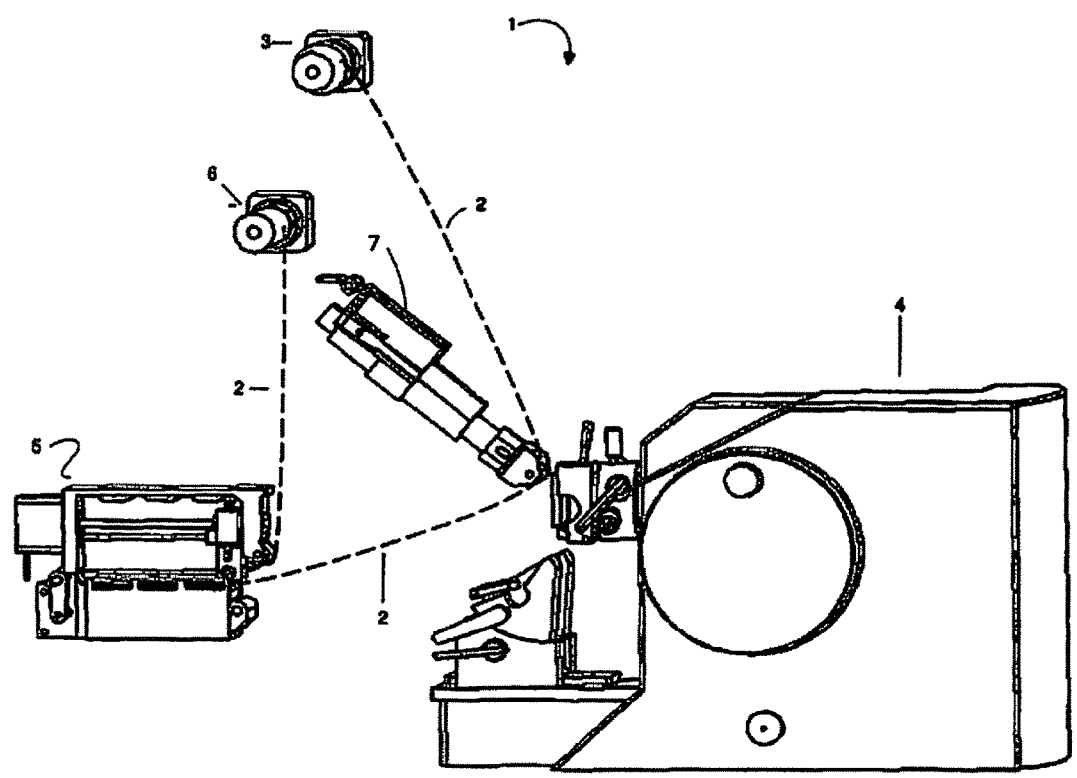
FIG. 1 is a schematic view of one embodiment of an automated tape transfer apparatus of the present invention, illustrating the path of the continuous tape.

The systems and methods of the disclosure may be further understood with reference to the following description and the appended drawings, wherein like elements throughout the views are referred to with the same reference numerals. The systems, methods and devices disclosed herein improve upon traditional microtomy. Specifically, they provide for using a continuous adhesive tape to support samples from tissue block cutting. The systems and methods also provide for subsequent transfer of the samples from the adhesive tape to slides.

A continuous strip of adhesive tape adheres to the cutting face of the sample block prior to sectioning. Subsequent to the adhesive tape adhering to the cutting face, the microtome begins a cutting action. The adhering of the adhesive tape to the cutting face supports the section that is being cut by the microtome. Once the microtome completes the cut, the section that has been cut remains adhered to the adhesive tape.

Motorized reels can be utilized to move the adhesive tape such that the adhesive tape does not interfere with the operation of the microtome. The motorized reels advance the adhesive tape so that the portion of the adhesive tape that includes the cut section moves away from the microtome and sample block and a new portion of the adhesive tape is positioned and adhered to the cutting face for the next section to be cut by the microtome and transferred to the adhesive tape. In the embodiments described below, the motorized reels are referred to as a feed mechanism and a take-up mechanism.

In some embodiments, the portions of the adhesive tape that include the cut sections are moved by the motorized reels towards a slide station where the section that is adhered to the adhesive tape may be automatically transferred to a slide. In some embodiments, the adhesive tape including the section is positioned over a slide that is coated with an ultraviolet ("UV") curable adhesive. A roller may then press the section on the adhesive tape onto the slide. A UV light source activates the UV adhesive on the slide, thereby bonding the section to the slide. Finally, the motorized reels advance the adhesive tape away from the slide and the section is no longer adhered to the adhesive tape, but is now bonded to the slide.

The systems and methods of the present invention will now be described in greater detail. It should be understood that the term "adhesive tape" as used above and used below throughout this specification refers to any type of bonding, including molecular bonding, mechanical bonding, etc., and also can include dry adhesive tapes such as Setex-dA produced by nanoGriptech which provides bonding via van der Waals force (molecular bonding) and whose tape peel force varies greatly on peel angle which minimizes section damage during peeling. It should also be noted that the term "continuous strip of adhesive tape" or "continuous" is used above and used throughout the specification. It would be understood by one of ordinary skill in the art that this term does not mean that the strip of adhesive tape is infinitely continuous. Rather, continuous means that the tape is longer than the amount of adhesive tape used for a single section (a single sample of tissue cut from the tissue block). For example, the tape could have a relative short length or could have a length that could be used for hundreds or thousands of sections. One example of a length of adhesive tape will be described below.

It should also be noted that the term "section" or "sections" is used extensively throughout this description. As described above and as will be described in more detail below, a microtome cuts sections from a sample block of tissue. Thus, the term "section" refers to the thin sample of tissue that has been or will be cut from the sample block and is adhered to the adhesive tape. Finally, as described above, the section is cut from the sample block by a microtome. This process is interchangeably referred to in this description as "cutting" or "sectioning" and should be understood to refer to the same process.

FIG. 1 is a schematic view of one embodiment of an automated tape transfer apparatus (system) 1, illustrating the path of the continuous adhesive tape 2. FIG. 1 shows a microtome 4 that is used to hold the sample blocks and cut the sections. As described above, the microtome 4 holds a sample block comprising a tissue sample that is enclosed in a supporting block of embedding material such as paraffin wax. The microtome 4 includes a blade (not shown) aligned for cutting slices (or sections) from one face of the tissue block. This face from which the section will be cut will be referred to herein as the cutting face and will be described in greater detail below. The blade of the microtome 4 cuts the sample block to create sections. The sections are very thin, e.g., 4 µm, although other dimensions are also contemplated, thus, a single sample block, for example a sample block having a thickness of 12 mm, may be cut into many sections (e.g., hundreds of sections).

In some embodiments, the paraffin block face could be cooled down and humidified. Cooling down the paraffin block helps increase the hardness of the medium. Harder paraffin blocks can be cut at a given thickness more consistently. Humidification of the tissue and the paraffin blocks helps to avoid tissue crumbling.

It should be noted that the microtome 4 may not be a portion of the automated tape transfer apparatus (system) 1. In some embodiments, the automated tape transfer apparatus 1 is an apparatus that may be attached to any standard microtome as an add-on component. However, in other embodiments, the microtome 4 may include an integrally attached automated tape transfer apparatus 1. That is, the automated tape transfer apparatus 1 may include the microtome 4 or may be a separate component that is attached or coupled to any microtome to provide the functionality described herein. In addition, the microtome 4 may be any type of microtome 4 including a rotary microtome, a lathe microtome, a sledge type microtome, a vibrating microtome, a laser microtome, etc. In any embodiment, (e.g., where the microtome is a component of the automated tape transfer apparatus or where the microtome is a separate component), the microtome may be a commercially available microtome or a specially designed microtome for use with the automated tape transfer apparatus 1.

Figure 23:
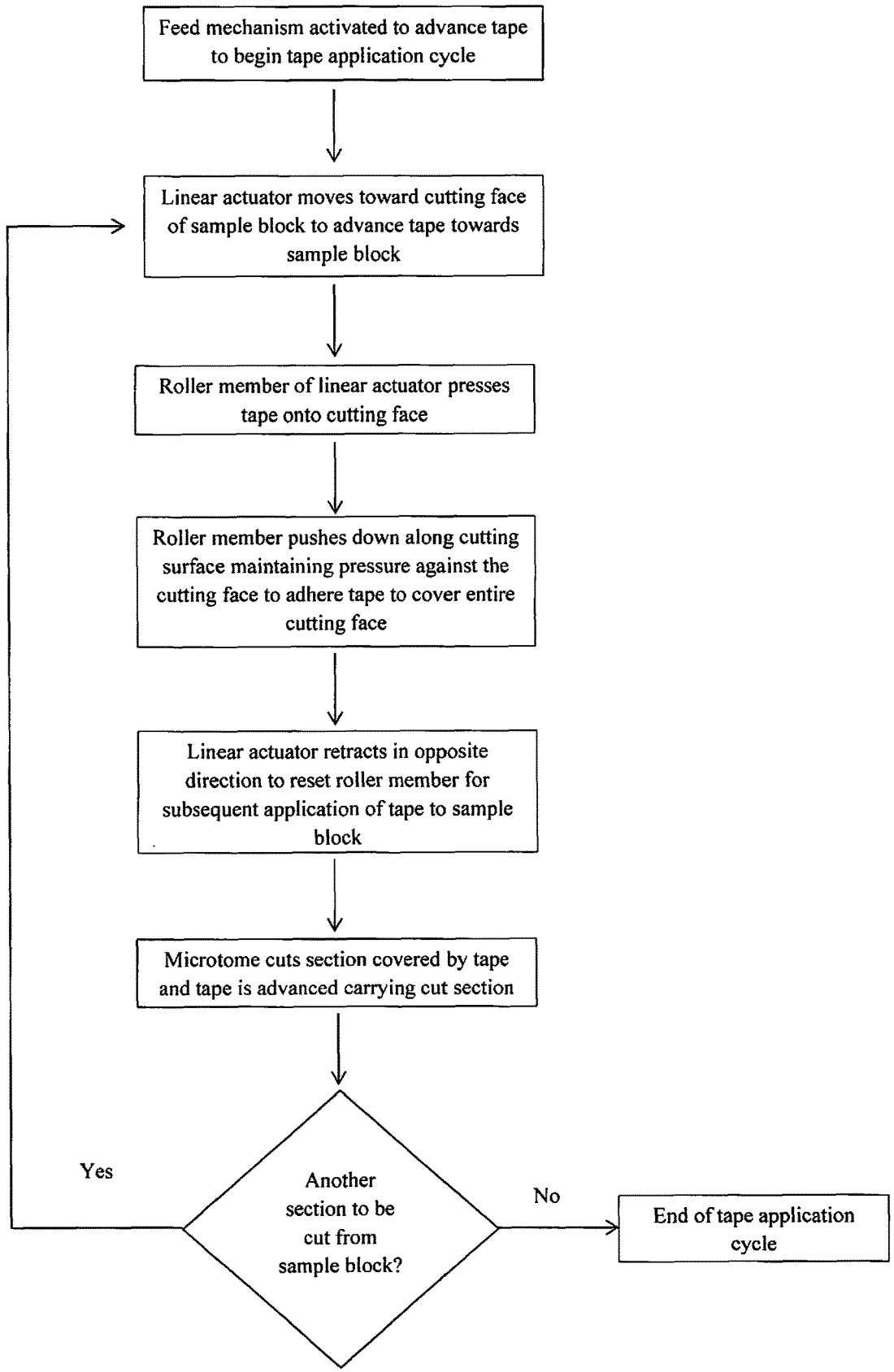
FIG. 23 is a flow chart illustrating the steps of an automated system for applying a sample to a tape in accordance with one embodiment of the present invention.

In addition to the adhesive tape 2 and the microtome 4, the automated tape transfer apparatus 1 of FIG. 1 also includes a feed mechanism 3, a tape applicator 7, a slide station 5 and a take-up mechanism. Each of these components and their functionality will be described in greater detail below. It should be appreciated that although slide station 5 is shown as part of system (apparatus) 1, it is also contemplated that the automated transfer system (apparatus) does not include a slide station. The flow chart of FIG. 23 depicts such system.

In the embodiment of FIG. 1, the path of the adhesive tape 2 starts at the feed mechanism 3 and travels toward the microtome 4 and an applicator end of the tape applicator 7. The adhesive tape 2 then travels away from the microtome and toward the slide station 5 and finally is stored on the take-up mechanism 6.

In one embodiment, the adhesive tape 2 comprises a flexible carrier film that has an adhesive material deposited thereon. The flexible carrier film has properties that resist tearing or stretching while remaining flexible as the adhesive tape moves through the automated tape transfer apparatus 1. In one embodiment by way of example, the adhesive tape 2 comprises a 1-inch (25.4 mm) wide, 1.5 mil (0.0381 mm) thick polyimide film coated with 1.0 mil (0.0254 mm) thick silicone adhesive. However, it should be noted that this is only one example and other materials, widths, and thicknesses may be used depending on the particular implementation, e.g., type of microtome, type of sample, etc. In some embodiments, the adhesive layer remains laminated to the flexible carrier film throughout the entire process, while in other embodiments, the adhesive layer may be dissolved or removed at the slide station to allow the transfer of the section to the slide. These various embodiments will be described below. The adhesive region of the adhesive tape 2 is preferably large enough to fully cover the cutting face of the sample block, i.e., to hold a complete section when it is sliced from the sample block.

In another embodiment, the adhesive layer on the adhesive tape 2 is a thermoplastic layer commonly and functionally known as a hot melt adhesive. The hot melt adhesive is a non-tacky solid at the ambient temperature within the automated tape transfer apparatus 1. After application to the cutting face, the hot melt adhesive is melted by heat. The adhesive tape 2 is bonded to the cutting face upon adhesive cooling it back to solid. The hot melt adhesive has a melting point below the temperature at which the embedding medium entirely melts. The exemplary bond strength should be the same as with the adhesive layer. Some examples of the hot melt adhesive may include polyester wax (having a melting point of 39 degrees C.) and DuPont Elvax 40W (having a melting point of 47 degrees C.).

In one example, the adhesive tape 2 is provided on a tape carrier that includes a tape roll that is 36.0 yards (32.9 m) of tape wound on a hollow cylindrical core. In one example, a diameter of the hollow cylindrical core is 3.0 in. (76 mm). However, this is only one example and other sizes may be used. When the adhesive tape 2 is rolled on the tape roll, the adhesive layer faces inward. The tape carrier may have sprocket holes or other mechanical means that allow the tape carrier to be coupled to the feed mechanism 3 and allow the feed mechanism 3 to feed the adhesive tape 2 through the automated tape transfer apparatus 1. In one embodiment, the adhesive tape 2 further includes an optional peel-able, non-adhesive liner covering the adhesive material that is to be removed before use. For example, when on the tape carrier, the non-adhesive liner may cover the adhesive, but as the adhesive tape 2 moves away from the feed mechanism 3, the non-adhesive liner may be removed by the automated system to expose the adhesive region of the adhesive tape 2. In this example, if it were to be assumed that each section had a section length of 28 mm and the automated tape transfer apparatus 1 was controlled such that there was a 10 mm spacing between each successive section, the exemplary length of adhesive tape 2 (e.g., a tape roll having a length of 36.0 yards (32.9 m)) would allow for the transfer of 865 sections per roll. Again, this is only one example of a length of a tape roll as other lengths may be used. In addition, the section length and section spacing is provided by way of example and other section lengths and spacings could also be utilized.

Figure 2:
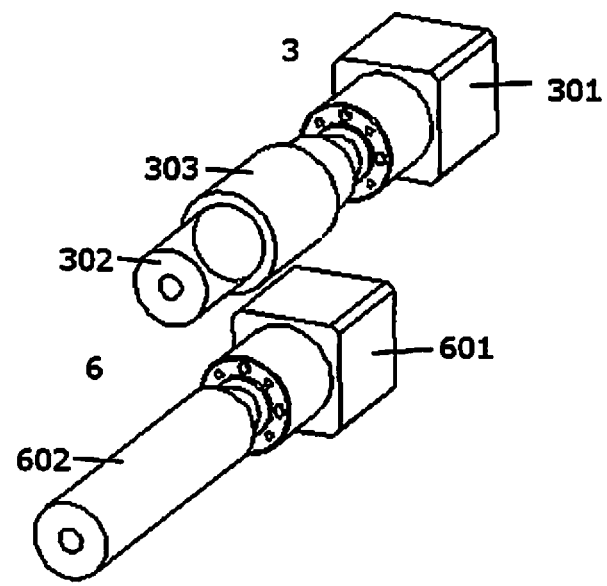
FIG. 2 shows a feed mechanism and a take-up mechanism of the automated tape transfer apparatus of FIG. 1 in more detail.

FIG. 2 shows the feed mechanism 3 and the take-up mechanism 6 of the automated tape transfer apparatus 1 in more detail. The feed mechanism 3 includes a coupling 303 that allows the tape carrier to be coupled to the feed mechanism 3. As described above, the tape carrier may include mechanical structure that allows for the coupling, e.g., sprocket holes, such that the coupling 303 may have a corresponding coupling structure. In other exemplary embodiments, the coupling 303 may be sized such that the tape carrier is pressure fit over the coupling 303. From these examples it should be seen that other structure/methods of coupling the tape roll to the feed mechanism 3 may be used. The feed mechanism 3 also includes a drive shaft 302 that is coupled to a motor 301. The motor 301 may be programmable or controlled by an external controller such that the motor 301 drives the drive shaft 302 so that the adhesive tape 2 is advanced through the automated tape transfer apparatus 1 at a speed that allows for the sections to be transferred to the adhesive tape 2 and then transferred to the slides (in the embodiments including the slide station). As will be described in greater detail below, the motors of the feed mechanism 3 and the take-up mechanism 6 may be controlled to account for various motions of the adhesive tape 2 along its path, including the speed for the correct distance between sections, slack that may occur during adhesive tape 2 movement, etc.

Similar to the feed mechanism 3, the take-up mechanism 6 also includes a drive shaft 602 and a motor 601. The motor 601 may also be programmable or controlled such that it is synched with the motor 301 allowing the adhesive tape to move through the automated tape transfer apparatus 1. The adhesive tape 2 that has been used (e.g., has moved through the slide station 5) may be rolled up onto the drive shaft 602. In an alternative embodiment, there may be a tape carrier that is coupled to the take-up mechanism 6 such that the used adhesive tape 2 is rolled onto the tape carrier coupled to the take-up mechanism 6.

Figure 3:
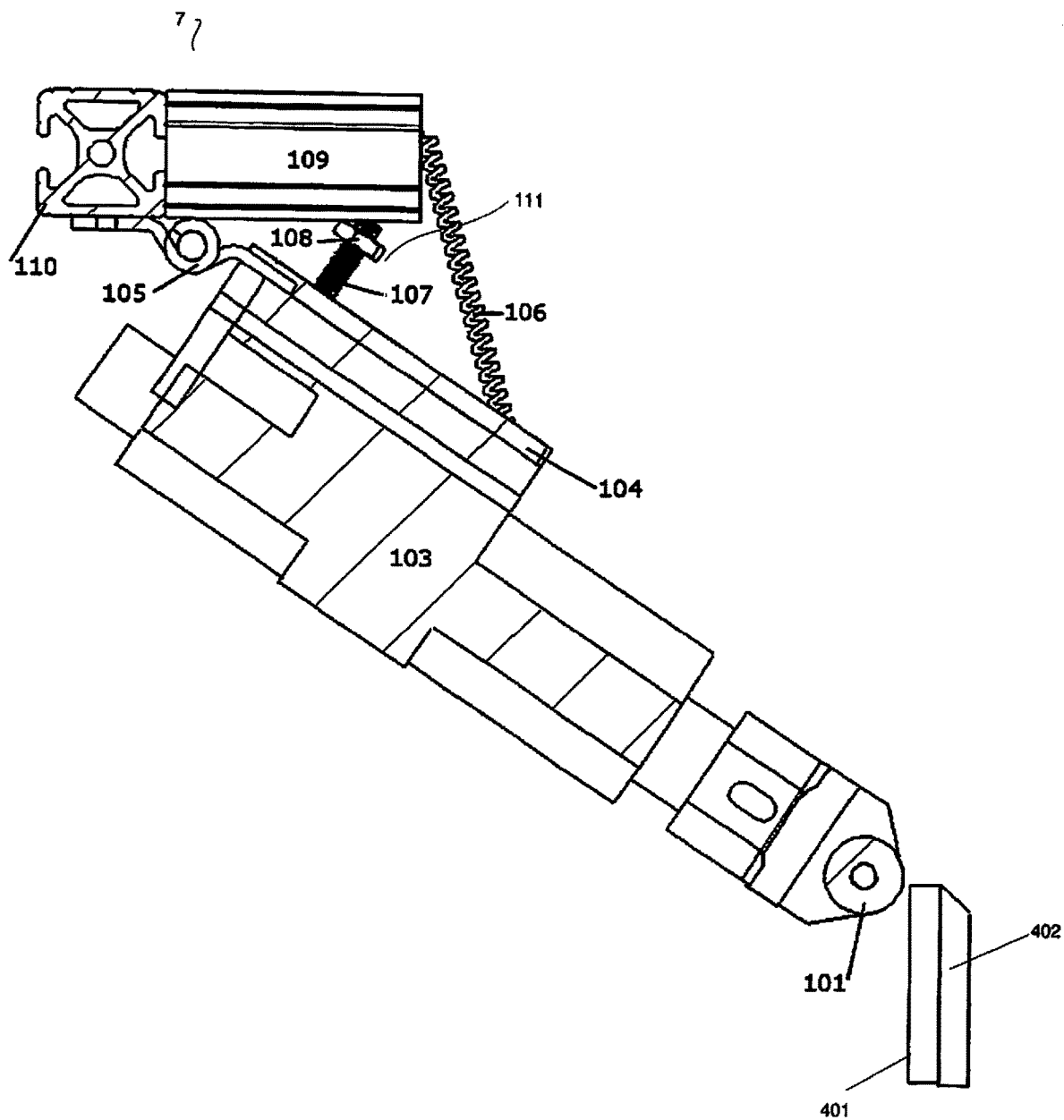
FIG. 3 shows a tape applicator of the automated tape transfer apparatus of FIG. 1 in more detail.

FIG. 3 shows the tape applicator 7 of the automated tape transfer apparatus 1 in more detail. FIG. 3 also shows a cutting face 401 of the sample block 402 from which the tissue section is to be cut. As described above, the sample block 402 is held by the microtome 4, which is not shown in FIG. 3 for ease of illustration. The interaction between the cutting face 401 and the tape applicator 7 will be described in greater detail below. The tape applicator 7 includes a roller member 101, or alternatively a cam, that extends from a linear actuator member 103 that pivots on a hinge member 105. The hinge member 105 is coupled to a linear actuator holder 104 and a fixed structural member 110. The hinge member 105 may be any type of hinge, e.g., butt hinge, t-hinge, strap hinge, etc. The fixed structural member 110 may be, for example, a subsection of the supporting structural framing of the automated tape transfer apparatus 1. The fixed structural member 110 and the hinge member 105 limit the range of motion of the roller member 101 to one degree of rotational freedom around the pivot of the hinge member 105 and one degree of translational freedom along the linear actuator holder 104 as will be described in greater detail below (e.g., as shown by arrow 120 in FIGS. 5 and 7).

The tape applicator 7 maintains an initial position via force from a spring member 106 that connects the linear actuator holder 104 to a second fixed structural member 109. Again, the second fixed structural member 109 also may be, for example, a subsection of the supporting structural framing of the automated tape transfer apparatus 1. A motion limiting member 111 maintains this initial position. In one embodiment, the motion limiting member 111 includes a nut 108 on a bolt 107, wherein the nut 108 acts as an adjustable limiter. However, other arrangements may be used to implement the motion limiting member 111.

The operation of the tape applicator 7 will be described with reference to an adhesive tape application cycle. The adhesive tape application cycle is the process by which the adhesive tape 2 is adhered to the cutting face 401. Prior to the beginning of each adhesive tape application cycle (e.g., when the next portion of adhesive tape 2 is to be applied to the cutting face 401), the linear actuator member 103 begins in a retracted position such that the roller member 101 clears the cutting face 401 as shown in FIG. 3.

Figure 4:
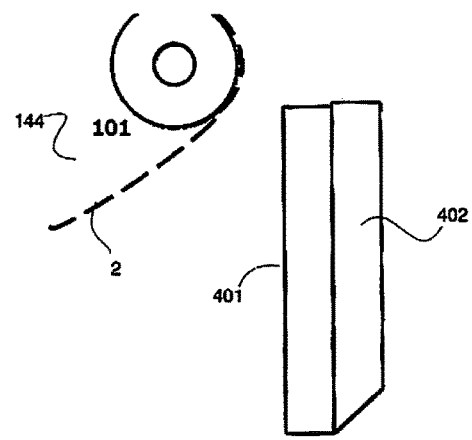
FIG. 4 shows a view of the roller member of the tape applicator of FIG. 1 and its relation to a cutting face prior to the beginning of an adhesive tape application cycle.

FIG. 4 shows another view of the roller member 101 of the tape applicator 7 and its relation to the cutting face 401 prior to the beginning of the adhesive tape application cycle. FIG. 4 also shows the adhesive tape 2 and its relation to the roller member 101 prior to the beginning of the adhesive tape application cycle.

Figure 6:
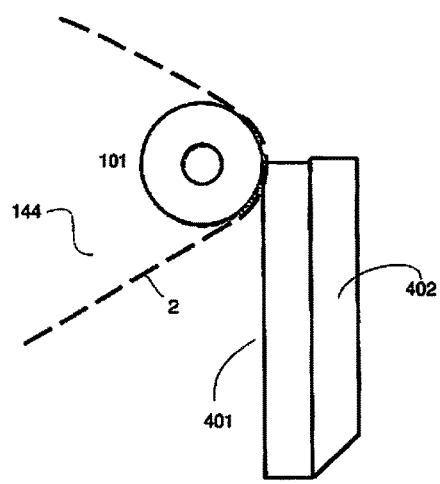
FIG. 6 shows a view of the roller member of the tape applicator of FIG. 1 and its relation to the cutting face of the sample block at the beginning of the adhesive tape application cycle.
Figure 5:
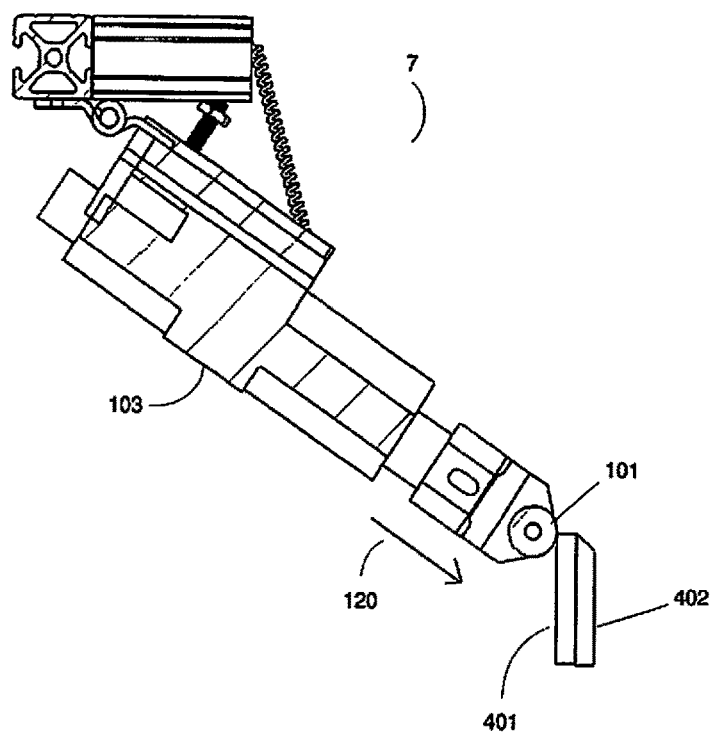
FIG. 5 shows the operation of the tape applicator of FIG. 1 as the adhesive tape application cycle begins.

FIG. 5 shows the operation of the tape applicator 7 as the adhesive tape application cycle begins. As the adhesive tape application cycle begins, the linear actuator member 103 elongates in the direction of arrow 120 towards the cutting face 401. This causes the roller member 101 to press the adhesive side of the adhesive tape 2 onto the cutting face 401. FIG. 6 shows another view of the roller member 101 of the tape applicator 7 and its relation to the cutting face 401 at the beginning of the adhesive tape application cycle. As can be seen in FIG. 6, the adhesive side of the adhesive tape 2 is now in contact with the cutting face 401. Also seen in FIG. 6, adhesive tape 2 below the roller member 101 in the area 144 becomes taut to prevent air pockets between the adhesive tape 2 and the cutting face 401 when the adhesive tape 2 is applied to the cutting face 401. The function of causing the adhesive tape 2 to become taut may be performed by the take-up mechanism 6. It should be noted that in FIG. 4, the adhesive tape 2 may not be as taut in the area 144 as it is in FIG. 6.

Figure 8:
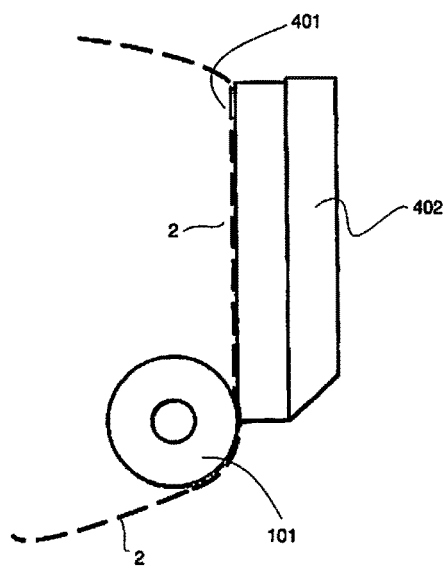
FIG. 8 shows a view of the roller member of the tape applicator of FIG. 1 and its relation to the cutting face of the sample block near the end of the adhesive tape application cycle.
Figure 7:
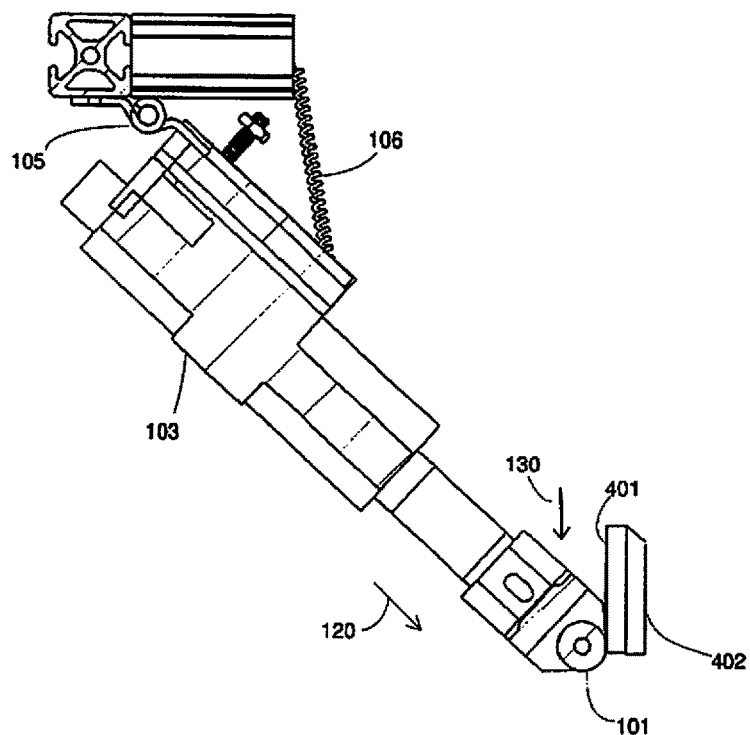
FIG. 7 is a view similar to FIG. 5 showing the operation of the tape applicator of FIG. 1 through the adhesive tape application cycle.

FIG. 7 shows the operation of the tape applicator 7 through the adhesive tape application cycle. With the sample block 402 firmly held in the microtome 4, further elongation of the linear actuator member 103 in the direction 120 forces the tape applicator 7 to pivot on the hinge member 105 and elongate the spring member 106. The force from the extending linear actuator member 103 pushes the roller member 101 down in the direction of arrow 130, while maintaining the pressure against the cutting face 401, e.g., there is a force applied by the roller member 101 that is normal to the cutting face 401. This movement by the roller member 101 against and down the cutting face 401 causes the adhesive tape 2 to adhere and cover the entire cutting face 401 with adhesive tape 2. FIG. 8 shows a view of the roller member 101 of the tape applicator 7 and its relation to the cutting face 401 when the linear actuator member 103 has extended fully such that the roller member 101 has contacted and moved along the entirety of the cutting face 401. Thus, the adhesive tape 2 is now adhered to the entirety of the cutting face 401.

The linear actuator member 103 is then retracted in the opposite direction of arrow 120 of FIGS. 5 and 7. This retraction causes the roller member 101 to reset to the original position as shown in FIG. 3 where the roller member 101 is clear of the cutting face 401. It should be understood that as the linear actuator member 103 is retracted, the spring force of the spring member 106 causes the hinge member 105 to rotate back to its original position. The hinge is stopped from moving at its original position based on the setting of the motion limiting member 111. In this embodiment, the strength and initial length of the spring member 106 may be adjusted to provide the correct amount of force that the roller member 101 exerts against the cutting face 401. In addition, in the retracted position, the spring force serves to maintain the tension of the adhesive tape 2 within the automated tape transfer apparatus 1.

Figure 9:
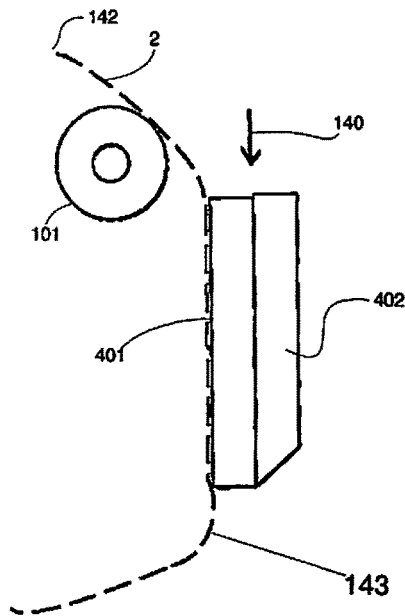
FIG. 9 shows a view of the roller member of the tape applicator of FIG. 1 and its relation to the cutting face when a linear actuator member of the tape applicator has been retracted at the end of the adhesive tape application cycle.

FIG. 9 shows a view of the roller member 101 of the tape applicator 7 and its relation to the cutting face 401 when the linear actuator member 103 has been retracted at the end of the adhesive tape application cycle. Comparing FIG. 4 to FIG. 9 it may be seen that the roller member 101 is in the same relative position. However, the difference is that in FIG. 9, the adhesive tape 2 is adhered to the cutting face 401, while in FIG. 4, the adhesive tape 2 is not adhered to the cutting block 401. It should be understood that the adhesive tape application cycle will progress from that as shown in FIG. 9 back to that shown in FIG. 4 when the microtome 4 cuts the section. That is, the microtome blade will cut the section from the sample block 402 and the section will remain adhered to the adhesive tape 2. The adhesive tape 2 will then pull away from the sample block 402 resulting in the adhesive tape 2 returning to the location as shown in FIG. 4. The automated tape transfer apparatus 1 may also include a controller (not shown) that communicates with the microtome 4 to indicate that the adhesive tape 2 has been adhered to the cutting face 401, e.g., as shown in FIG. 9. This will indicate to the microtome 4 that the section may be cut. It should be noted that the microtome 4 may have a limited logic input and programmability such that it may only receive a simple binary signal to begin cutting a section. In another example, the microtome 4 may have a more sophisticated controller that allows the microtome 4 and the controller of the automated tape transfer apparatus 1 to exchange more signals and data.

The microtome 4 will then advance the sample block 402 forward and this will define a new cutting face 401. The adhesive tape application process will then begin again for the next section. The section that has been previously cut from the sample block 402 and is now adhered to the adhesive tape 2 will then advance away from the microtome 4 toward the slide station 5. However, prior to describing the functionalities carried out by the slide station 5, a further description of the cutting of the section after the cutting face 401 has been adhered to the adhesive tape 2 will be described.

It should be noted that as the microtome 4 cuts the section, slack or other movement of the adhesive tape 2 may occur. For example, if the microtome 4 is a rotary type microtome, the cutting occurs by the sample block 402 being moved, rather than the blade moving. Thus, the automated tape transfer apparatus 1 may compensate for any movement of the adhesive tape 2 during the cutting process. For example, in the rotary type microtome, the sample block 402 will descend (e.g., move down in the direction of arrow 140 of FIG. 9), and the feed mechanism 3 may unwind slack stored on the tape roll above the cutting face 401 to prevent the adhesive tape 2 from peeling off the cutting face 401. Concurrently, the take-up mechanism 6 may wind excess adhesive tape 2 between the cutting face 401 and the microtome blade that may otherwise lead to jams, misalignments, and tape cuts by the microtome blade. As described above, the motors 301 and 601 of the feed mechanism 3 and take-up mechanism 6, respectively, may be a controllable motor that may be programmed with the functionality to account for the movement of the adhesive tape 2 during the cutting process. It should be noted that the example provided above includes the movement caused by a rotary microtome, but other types of microtomes may also be used and also cause movement of the adhesive tape 2 during the cutting process. Those skilled in the art will understand that this movement may also be compensated for using the principles described herein.

It should be noted that when the chuck of the microtome moves the sample block in the direction of arrow 140 of FIG. 9, there should be some slack in the adhesive tape 2 in the area 142 (e.g., above the roller member 101) because without slack, the adhesive tape 2 may peel from the cutting face 401 during the sectioning process. This slack also prevents the tape from stretching and breaking. In one exemplary embodiment, the slack buffer is about half the circumference of the reel of the feed mechanism 3 or approximately 135 mm. In another example, there should also be some slack in the area 143 shown in FIG. 9 for the same reasons as described above. This slack in the area 143 may be controlled by the take-up mechanism 6 and its corresponding components (e.g., motor 601). This slack in area 143 may be controlled such that the adhesive tape 2 does not peel during the sectioning process, but also so the adhesive tape 2 does not break or get tangled within the automated tape transfer apparatus 1.

Some properties of the adhesive tape 2 were described above, however, some additional properties of the adhesive tape 2 will also be described. In addition to the functionality of automatically moving the section from the cutting face 401 to the slide station 5, the adhesive tape 2 also provides support to the section and cutting face 401 as the section is being cut by the microtome 4. Thus, the adhesive properties of the adhesive tape 2 should withstand the sectioning process without delamination, yet, later release the section without damage during following transfer to a slide at the slide station 5. Proper adhesion between the adhesive tape 2 and the cutting face 401 is based on a clean, flat cutting face 401 and complete penetration of the support medium (e.g., the paraffin) into the tissue. For tissue with solid regions devoid of a support medium, a minimum adhesive strength should also extend to the tissue. In one embodiment, an adhesion force of 10 ozf.-in. (0.071 Nm) between adhesive tape 2 and the cutting face 401 is a minimum adhesive strength for reliable, uniform adhesive tape 2 support. The maximum adhesive strength of the tape during the peel (at the slide station 5) should not exceed the tissue-dependent elastic limit of the section, defined as the minimum force that permanently deforms the section. There may be instances where the tissue elastic limit may dictate a maximum tape adhesive strength limit lower than the minimum tape adhesive strength required for sectioning. A solution to this issue will be described in greater detail below in the context of section transfer to a slide. It should be noted that while the above describes an example of a minimum adhesive strength for the adhesive tape 2, this example of minimum adhesive strength is based on tests that have been performed using various sample blocks and microtomes. There may be situations where the minimum adhesive strength is greater or less than the exemplary minimum adhesive strength described above.

In addition, the adhesive material used for the tape should be sufficiently viscous to limit section translation on the tape, e.g., when the section is subject to transverse friction force against the cutting blade during sectioning. Furthermore, viscous adhesive reduces residue on the section after the adhesive tape 2 is peeled during transfer to a slide.

In another embodiment, the microtome blade may be heated to aid in sectioning. A heating element, such as a heating pad, placed in close proximity to the blade may be used to for heating. In traditional sectioning without the adhesive tape 2, heating of the blade may result in undesirable curing or softening of the embedding medium (e.g., the paraffin). However, the support provided by the adhesive tape 2 at the cutting face 401 counters these issues. In cases where the embedding medium comprises a polymer such as paraffin, a hot blade locally melts a fraction of the supporting medium with lower melting points. For example, the paraffin may completely melt at 57 degrees C. However, when heated to 45 degrees C., the paraffin "sweats" as a fraction of polymers melt. At 45 degrees C., the paraffin will still generally behave as a solid, but be much softer than cool paraffin. This melted material lubricates the blade during the cut, reducing mechanical damage to the section. The remaining softer solid fraction also sections easier. The range of blade temperatures will depend on the melting point and heat capacity of the embedding medium, as well as the cutting speed. For an exemplary paraffin embedded block that completely melts at 57 degrees Celsius sectioned at 1 in/s (2.54 cm/s) for 4 μm thick sections, an exemplary blade temperature is approximately 42-48 degrees Celsius.

Those skilled in the art will understand that the above discussion is related to a situation when the embedding medium is paraffin and relates to the plastic properties of paraffin. Specifically, the plastic properties of solid paraffin change throughout a thermal range. For example, when paraffin is subjected to some specific compressive, tensile, or shearing force at different temperatures, a different type of response occurs above or below some critical temperature that may be termed the "plastic point." However, it will be recognized that other embedding mediums may also be used and these other embedding mediums may also have various thermal characteristics, e.g., plastic points. The heating of the blade may be modified to account for the plastic properties of these other types of embedding mediums.

Figure 10:
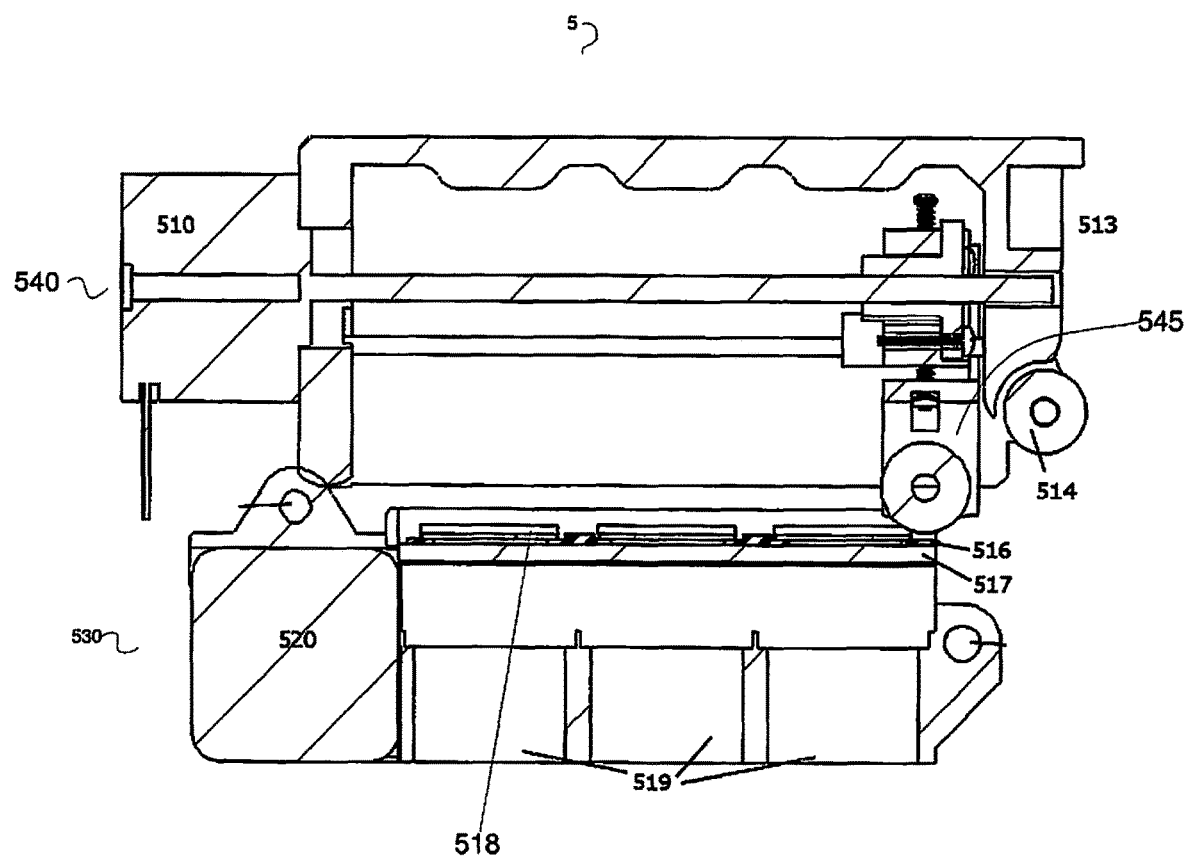
FIG. 10 shows one embodiment of a slide station of the automated tape transfer apparatus of FIG. 1.

FIG. 10 shows the slide station 5 of the automated tape transfer apparatus 1 in more detail. In the exemplary embodiment, the slide station 5 will be described as a UV station, but those skilled in the art will understand that it is not required that the slide station 5 be a UV station. The slide station 5 transfers the sections that are on the adhesive tape 2 to microscope slides 515 that are pre-coated with UV-curable adhesive. It should be appreciated that although the system of FIG. 1 includes a slide station for transfer to slides, the system in some embodiments does not include a slide station and after transfer of the cut sections to the adhesive tape and movement of the tape from the microtome area, the sections can be transferred from the adhesive tape to the slides in accordance with other methods, e.g., manual transfer. This is depicted in the flow chart of FIG. 23.

Figure 14:
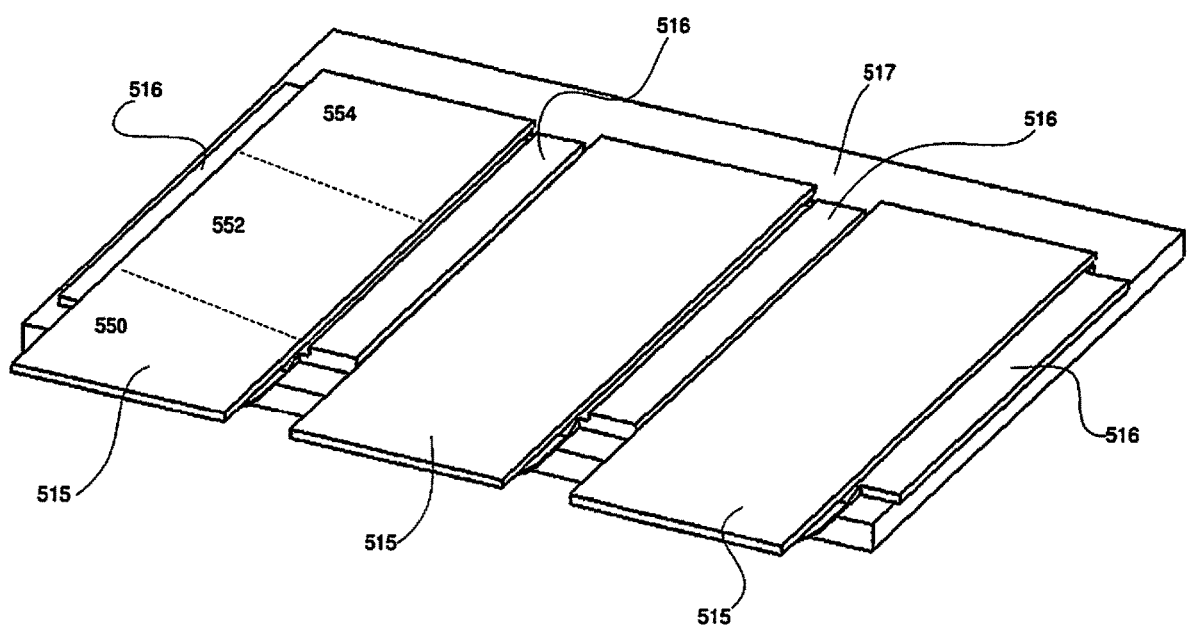
FIG. 14 shows a view of slides in the lower portion of the slide station of FIG. 10.

Turning now to the slide station 5 in more detail, a lower portion 530 of the slide station 5 includes spacers 516 that create the slide slots, a support section 517, a UV source 519 and a motor 520. The slide slots created by the spacers 516 and the support section 517 hold the slides 515. The spacers 516 may also limit contact with slides 515 by only contacting the sides and a tiny lip around the bottom of slides 515. In case the slides 515 have stray UV curable adhesive on the bottom/sides, the slides 515 may still be easily removed after UV exposure. The support section may be, for example, a glass plate that protects the UV source 519. In the present example, there are three slide slots with each slide slot holding a single slide 515. However, other exemplary embodiments may include more or less slide slots. It can be seen that the spacing between the sections on the adhesive tape 2 may be controlled based on the distances between the multiple slides 515 within the slide slots, e.g., the spacing should be such that in this example, a section may be simultaneously deposited on each of the slides 515. FIG. 14 shows a larger view of slides 515 in the lower portion 530 of the slide station 5. The slides 515 are shown as being held by the spacers 516 which are supported by the support section 517.

The UV source 519 is located below the slides 515 and as will be described in greater detail below, the UV source 519 is used to cure the UV adhesive, laminating the sections onto the slides 515. In one example, the UV source is an LED array. The motor 520 is used to translate or move the lower portion 530 of the slide station 5 to adjust the section location on a slide 515. That is, the exact location of where the sample section from the tape is deposited on the slide 515 may be controlled by the motor 520 moving the lower portion 530 to the desired location with respect to an upper portion 540 of the slide station 5.

In a normal situation, the sections from the adhesive tape may be deposited on the middle of the slide 515 (each section deposited on a sample slide). However, there may be situations where it is desired to deposit the section on a different portion of the slide that is not in the middle. For example, the user may desire to have multiple non-serial sections be collected onto a single slide 515. Thus, the motor 520 may adjust the location of the slide slots 516 such that a first section is deposited on the right portion (554 as shown in FIG. 14) of the three slides 515 in the slide slots 516. These deposited sections may then be cured using selective UV exposure by the UV source to only the area (e.g., the right portion of the slides) where the section has been deposited. The motor 520 may then move the lower portion 530 to a location where the next set of sections will be deposited in the middle (552 as shown in FIG. 14) of the slides 515. Thus, the same slides will be used for the next set of sections, but these sections will be deposited in the middle of the slides 515. The motor 520 may then move the lower portion 530 to a location where the next set of sections will be deposited on the left side (550 as shown in FIG. 4) of the slides 515. Thus, at the end of such a process, each of the three slides will have three non-serial sections deposited on each of the slides, e.g., one on the right side, one in the middle and one on the left side. In an alternative embodiment, the lower portion 530 may remain stationary and the upper portion 540 may be programmed to move and adjust position to deposit the sections in the manner described above. As can be appreciated, to adjust the position for multiple sections on a single slide, either the lower portion 530 or upper portion (or both relative to one another) can be moved in a direction transverse to the lengthwise dimension of the tape.

The upper portion 540 of the slide station 5 includes a translation portion 545, a track 509, a drive shaft 508 and a motor 520. As will be described in greater detail below, the motor 510 drives the drive shaft 508 such that the translation portion 545 moves along the track 509. The drive shaft 508 may be, for example, a screw drive that allows the translation portion 545 to move in either linear direction with respect to the lower portion 530.

Figure 11:
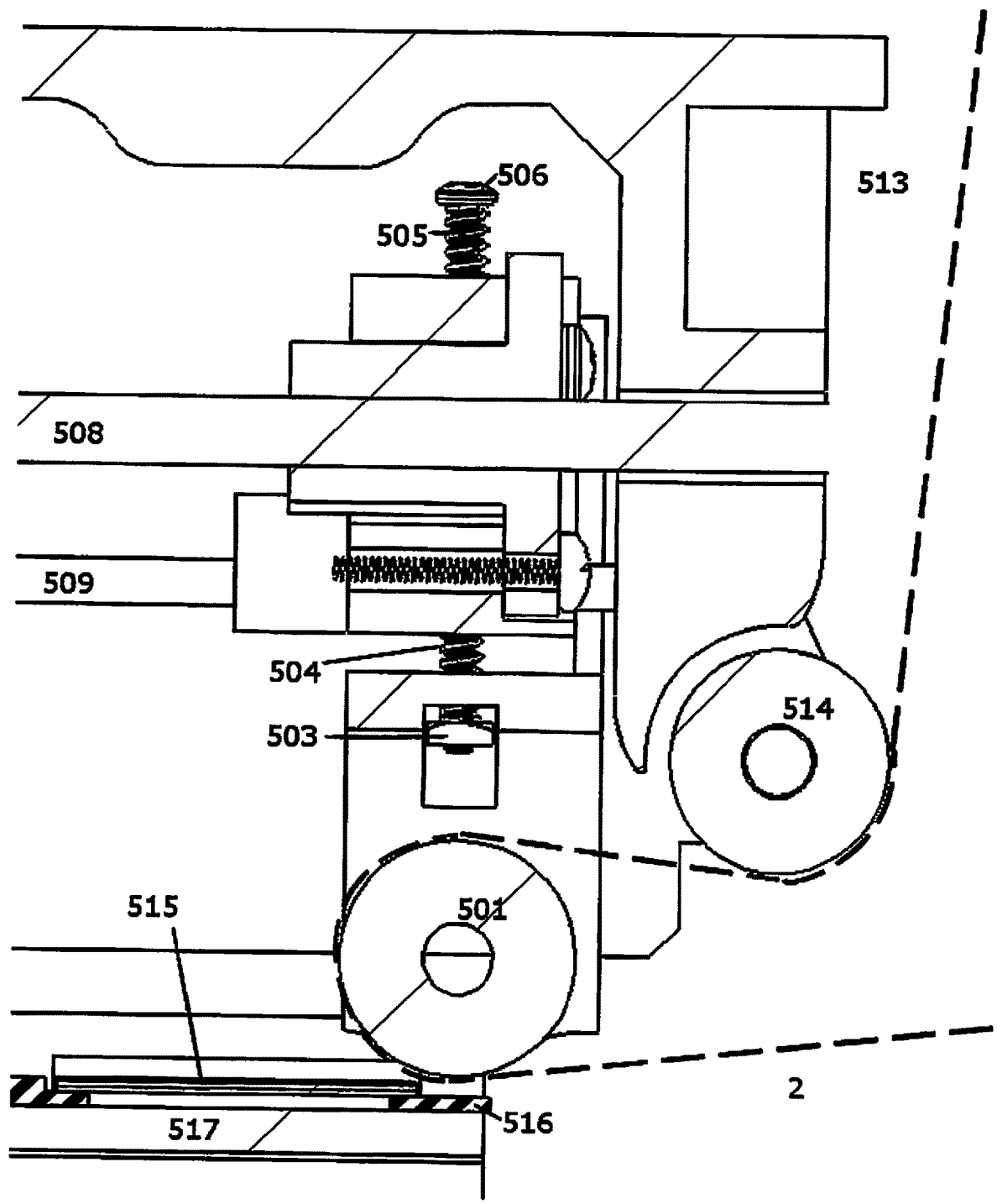
FIG. 11 shows a translation portion of the slide station of FIG. 10 in more detail.

FIG. 11 shows the translation portion 545 of the exemplary slide station 5 in more detail. The translation portion 545 includes a slide application roller 501. At the start of each cycle, the translation portion 545 is positioned on the end of track 509 closest to microtome such that the slide application roller 501 is in the location as shown in FIGS. 10 and 11. In this position, the slide application roller 501 is not in contact with the slides 515 allowing the adhesive tape 2 to advance. The adhesive tape 2 wraps around the slide application roller 501 with the non-adhesive film side of the adhesive tape 2 contacting the slide application roller 501. The adhesive film side can face toward the slide when positioned to be transferred. When the sections on the adhesive tape 2 are properly aligned with the receiving slides 515, the motor 510 may then drive the translation portion 545 to advance along the track 509. As the translation portion 545 advances along the track 509, the slide application roller 501 presses the sections that are adhered to the adhesive tape 2 onto the slides 515. The translation portion 545 may include springs 504 and 505 that work in conjunction with the slide application roller 501. The springs 504 and 505 may provide constant force onto adhesive tape 2 when applying sections to slides 515. The springs 504 and 505 may have their spring strength adjusted using screw 506 and nut 503. Alternatively, the slide application roller 501 may be made of a pliable material such as rubber foam that provides the constant force in lieu of the springs 504 and 505. In addition, a non-stick coating may be applied to the slide application roller 501 to prevent stray adhesive buildup and adhesive tape cling.

Figure 12:
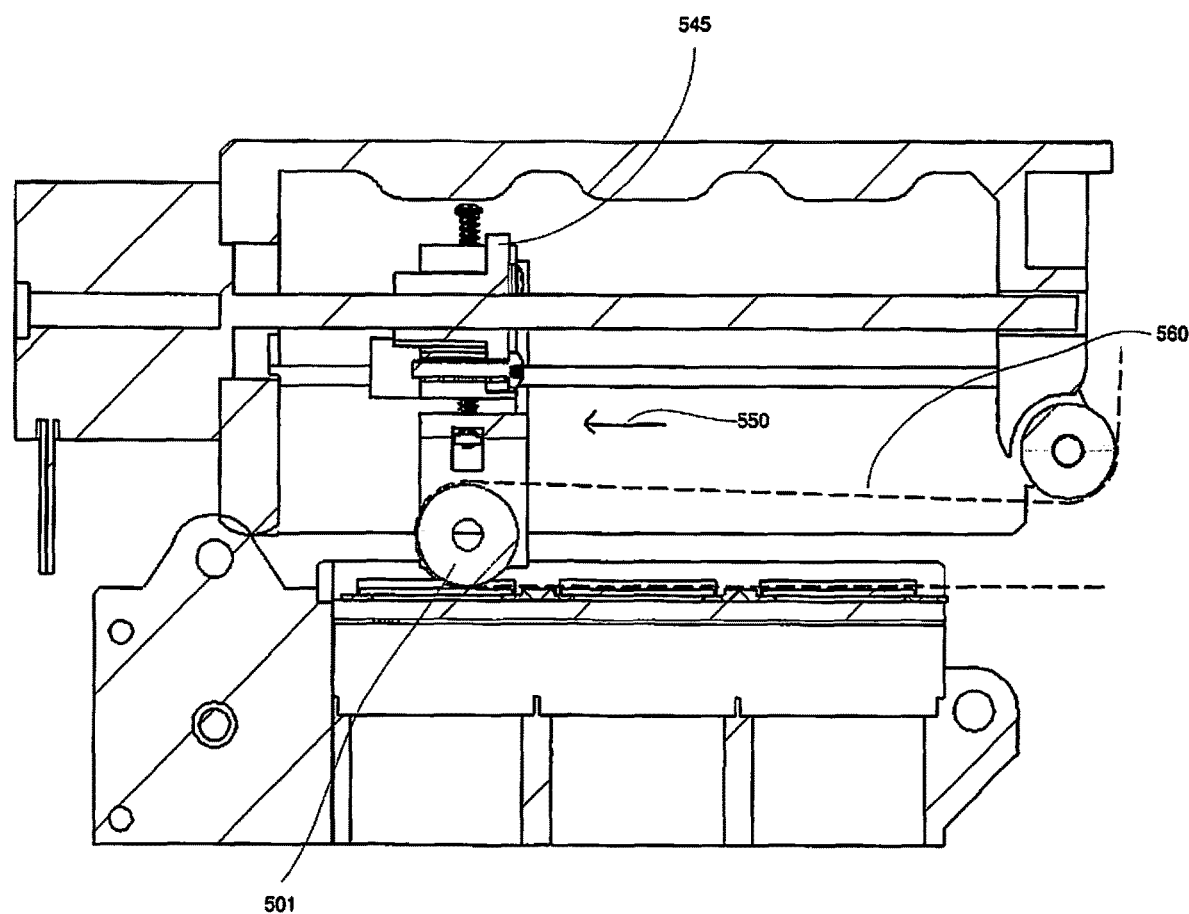
FIG. 12 shows the slide station of FIG. 10 when the translation portion has moved along a track and has applied sections to the slides.

FIG. 12 shows the slide station 5 when the translation portion 545 has moved along the track 509 in the direction of arrow 550, i.e., in a longitudinal direction and has applied sections to the slides 515. As the translation portion 545, including the slide application roller 501, is advancing in the direction of arrow 550, slack is applied from the take-up mechanism 6. For example, the section of adhesive tape 2 in the area 560 above the slide application roller 501 may be slack from the take-up mechanism 6. As the slide application roller 501 moves in the direction of arrow 550, this motion may laminate multiple regularly spaced sections and slides 515 in one pass. When the translation section 545 reaches the end of the track 509 near the motor 510, the adhesive tape 2 and therefore, the sections on the adhesive tape 2 have been deposited onto the slides 515. After slide section application, the UV source member 519 below the slides 515 cures the UV adhesive, laminating the deposited sections onto the slides 515. The translation portion 545 may then move back to its original position as shown in FIGS. 10 and 11. As the translation portion 545 moves back to its original position, the adhesive tape 2 is peeled away from the slide 515. As described above, the adhesive strength of the adhesive tape 2 should be such that when the peeling occurs, there is no damage to the section that has now been laminated on the slide 515. Finally, the expended adhesive tape collects on the take-up mechanism 6.

Figure 24:
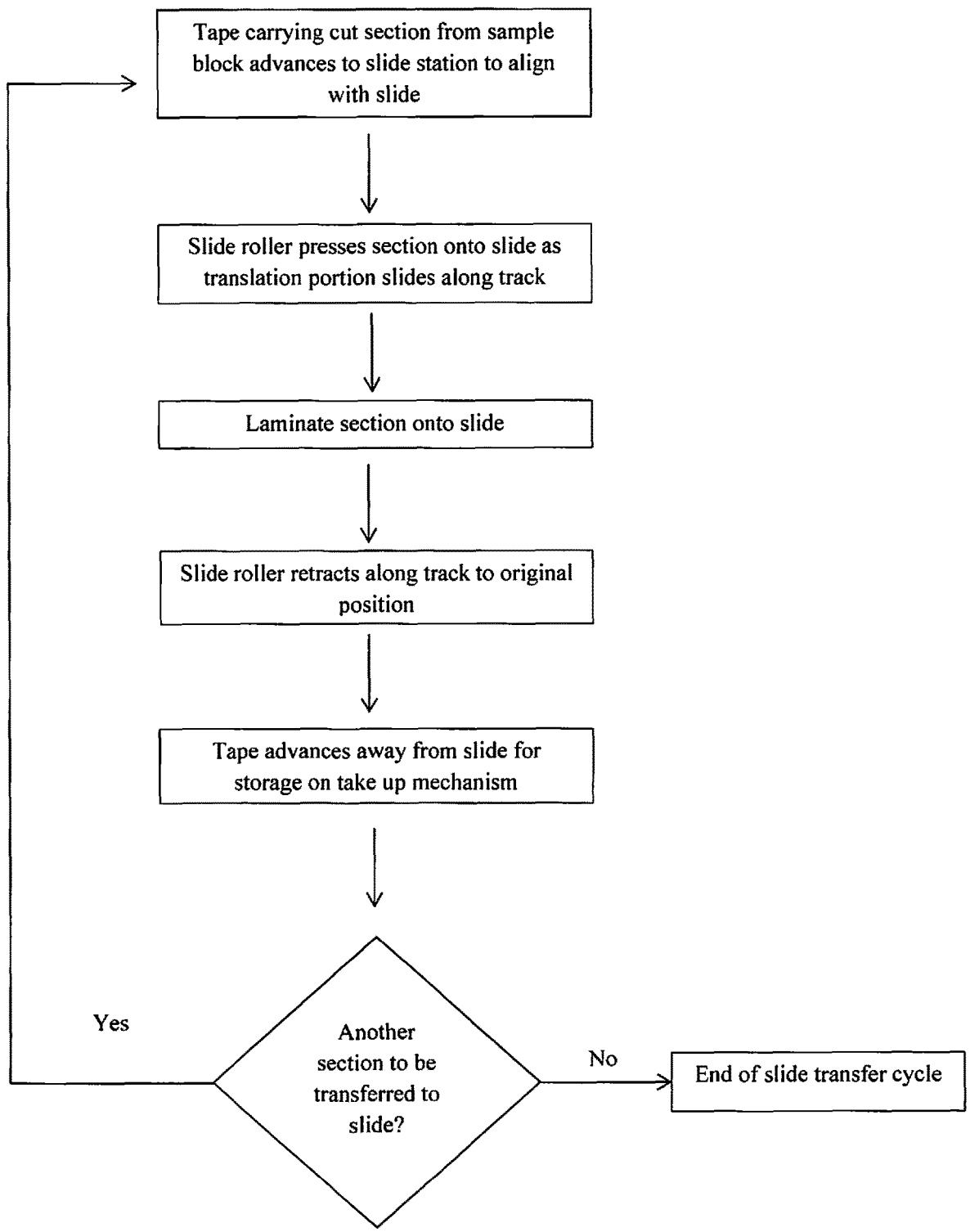
FIG. 24 is a flow chart illustrating the automated steps for transferring a sample from tape to a slide in accordance with one embodiment of the present invention.

It should be understood that the slide transfer system can be used with other systems than those disclosed herein to transfer cut sections from a tape onto slides. Such independent slide system is depicted in the flow chart of FIG. 24.

Returning to the curing process, in one embodiment, the UV source 519 has a peak wavelength of 375 nm and a UV dose of 30 mJ/mm2 is used to cure the adhesive. In one example, an exposure of 15 seconds at 4.3 W was applied evenly over a 3.0 in$^2$ (1940 mm$^2$) profile of each slide 515. In one example, the slides 515 are prepared with a custom UV curable adhesive coating. First, the slides 515 are treated with a transparent, uniform electrically charged coating to promote adhesion with cured UV adhesive. This may be accomplished by coating clean borosilicate microscope slides with a solution of cyanoacrylate diluted in acetone and drying. Next, a uniform 15 µm to 20 µm layer of UV adhesive is applied to the slide surface. If a viscous, non-self-leveling UV adhesive is used, the UV adhesive should be leveled. Again, this is just one example of a slide and a UV adhesive and UV exposure, there may be other manners of laminating the sections onto the slides.

These other manners of laminating the section onto the slide may include other types of adhesives that may be cured using other spectrums of light. In addition, the other types of adhesives may include adhesives that cure in other manners. An example of such an adhesive being used on the slide is provided below. Some exemplary characteristics of the exemplary adhesives that may be used to laminate the section to the slide is that the adhesive should be reasonably optically transparent (when cured if applicable), should match the refractive index of the slide glass (when cured if applicable) and should not react or interfere in later slide processing steps.

Figure 13:
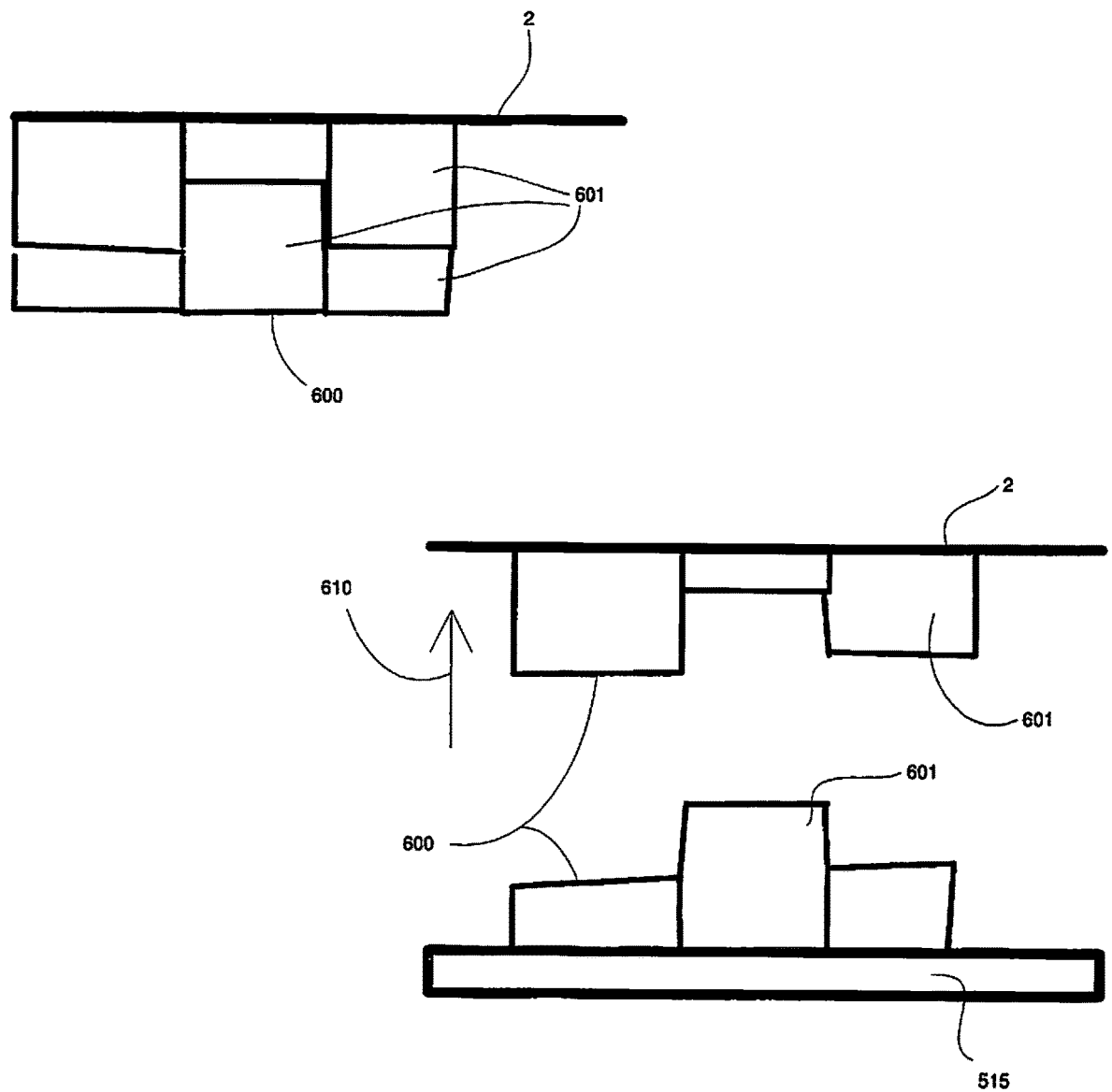
FIG. 13 is a schematic view showing an example of an incomplete section transfer from the adhesive tape to a slide.

FIG. 13 shows an example of an incomplete section transfer from the adhesive tape 2 to the slide 515. The left portion of FIG. 13 shows a section 600 that has been adhered to the adhesive tape 2. The section is shown as including a series of cells 601. Those skilled in the art will understand that the cells 601 may represent any material having internal cleavage planes/bonds that may be weaker than the bond with the adhesive tape 2. The right hand portion of FIG. 13 shows the section 600 being transferred from the adhesive tape 2 to the slide 515. In the right hand portion of FIG. 13, it may be considered that the section 600 has been deposited on the slide 515 and that the UV adhesive of the slide 515 has been cured. Thus, this is the time when the adhesive tape 2 is being peeled in the direction of arrow 610 from the slide 515 and section 600. In this example, the adhesive strength of the adhesive tape is greater than the adhesive strength of the UV adhesive of the slide 515, resulting in the section 600 being not completely transferred to the slide 515, e.g., the peeling of the adhesive tape 2 from the slide resulted in some of the cells 601 of the section 600 remaining on the adhesive tape 2. This is an incomplete transfer and an undesirable result. Thus, as described above, the maximum adhesive strength of the adhesive tape 2 should be such that it does not result in the incomplete transfer as shown in FIG. 13. However, as described above, there may be situations where the tissue elastic limit may dictate a maximum tape adhesive strength limit lower than the minimum tape adhesive strength required for sectioning. The following exemplary embodiments provide a solution for this issue.

In various embodiments, the adhesive strength of the adhesive tape 2 may be varied to expand the range of tissues transferable via the adhesive tape 2. In these embodiments, the tape adhesive strength is lowered immediately prior to peeling the adhesive tape 2 from the section so as not to exceed the section elastic limit. The tape adhesive strength may be reduced via heating, cooling, or UV exposure. That is, the particular adhesive that is used for the adhesive tape 2 may have properties that can be changed under certain conditions. Heating the adhesive tape 2 that has been laminated to the slide 515 may be done, for example, via radiative heating element, by a convective heating element for the enclosed slide transfer compartment, or by a conductive heating element. The radiative source may be incorporated into the UV adhesive curing light source 519. Heating the adhesive tape may also introduce issues with the sections such as melting the section embedding medium such as paraffin as was described above with respect to the heating of the microtome blade. Thus, the amount of heat should be controlled to reduce the adhesive strength of the tape, but not cause damage to the section.

For some tape adhesives such as silicone, cooling the adhesive leads to the desired weakened adhesive strength. Unlike the heating method, cooling will not promote melting of an embedding medium. In one example, a pressurized freezing spray may be used to reduce the adhesive temperature. In another example, the temperature of the slide application compartment within the slide station 5 may be lowered. Whether cooling or heating, the varying expansion or contraction between the section on slide 515 and adhesive tape 2 may also aid in delamination of the section from the adhesive tape 2. An adhesive tape 2, such as a UV dicing tape, which becomes less adhesive after UV exposure, may also be used. The UV source for reducing the tape adhesive strength may be a separate UV source or may be incorporated into the UV source 519 used for curing the slide UV adhesive. After the adhesive strength is lowered, the adhesive tape 2 may be more easily peeled from the sections, leaving the sections on the slides.

In the example of the adhesive tape 2 being a hot melt adhesive type tape, the regions of the hot melt adhesive supporting sections on the adhesive tape 2 may be melted prior to section transfer to the slides or alternatively during transfer to the slides. This procedure allows the sections to expand on the liquid layer akin to a water bath to reverse tissue compression caused during tissue processing and embedding prior to sectioning. Allowing the hot melt layer to cool fixes the expanded section in place. Transferring the section to the slide 515 may be with a UV curable adhesive. Alternatively as in the embodiment with UV release adhesive, heating the hot melt layer lowers the adhesion between section and adhesive tape 2 during tape peel. Cooling the tape-section-slide laminate post UV cure may likewise release the adhesive tape 2 from the section via differential thermal contraction. This method may allow a weaker viscous solution to replace the UV cure adhesive.

In another exemplary embodiment, the adhesive tape 2 may comprise a hot melt adhesive layer on a binding layer on a carrier layer. The binding layer more firmly adheres to a solid hot melt adhesive and carrier than the two layers to each other. The binding layer may be the aforementioned UV release adhesive. If so, UV exposure prior to tape peel may improve on-slide section retention.

Figure 18:
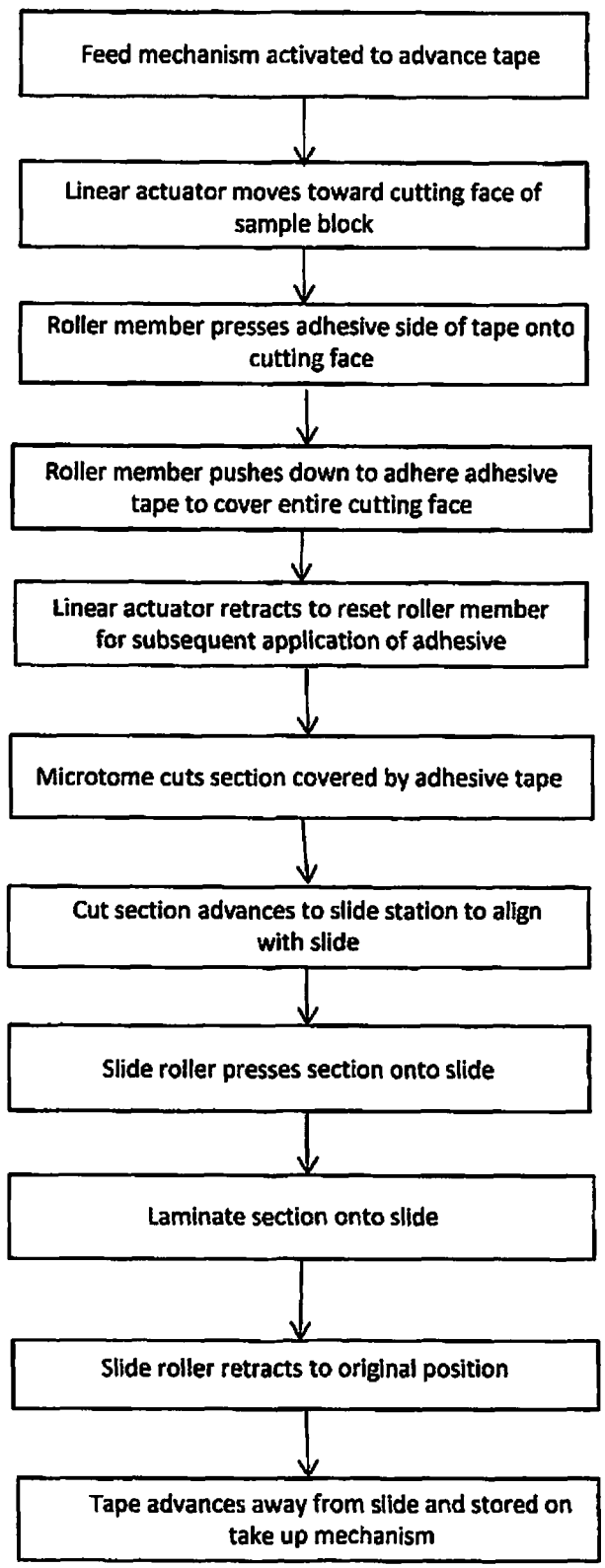
FIG. 18 is a flow chart illustrating the automated steps of the system of FIG. 1.
Figure 19:
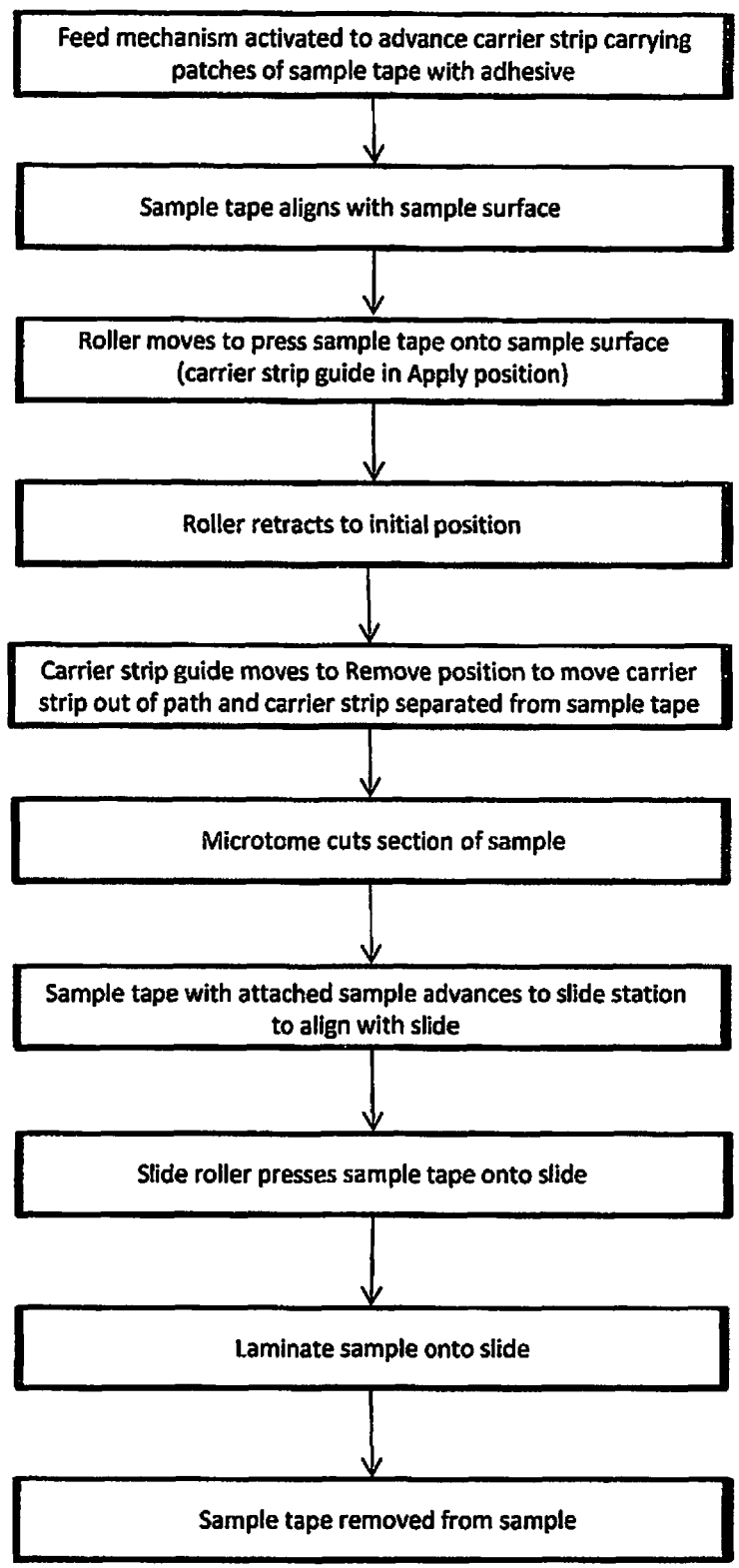
FIG. 19 is a flow chart illustrating the automated steps of an alternate system of the present invention.
Figure 21:
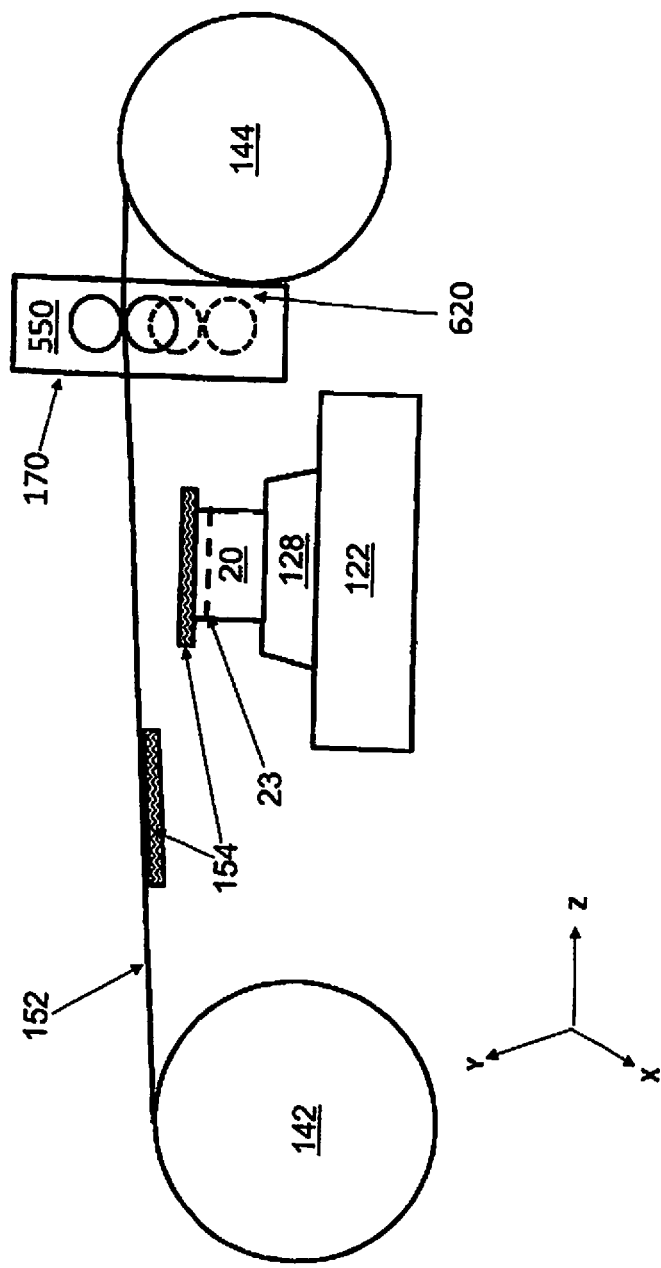
Figure 22:
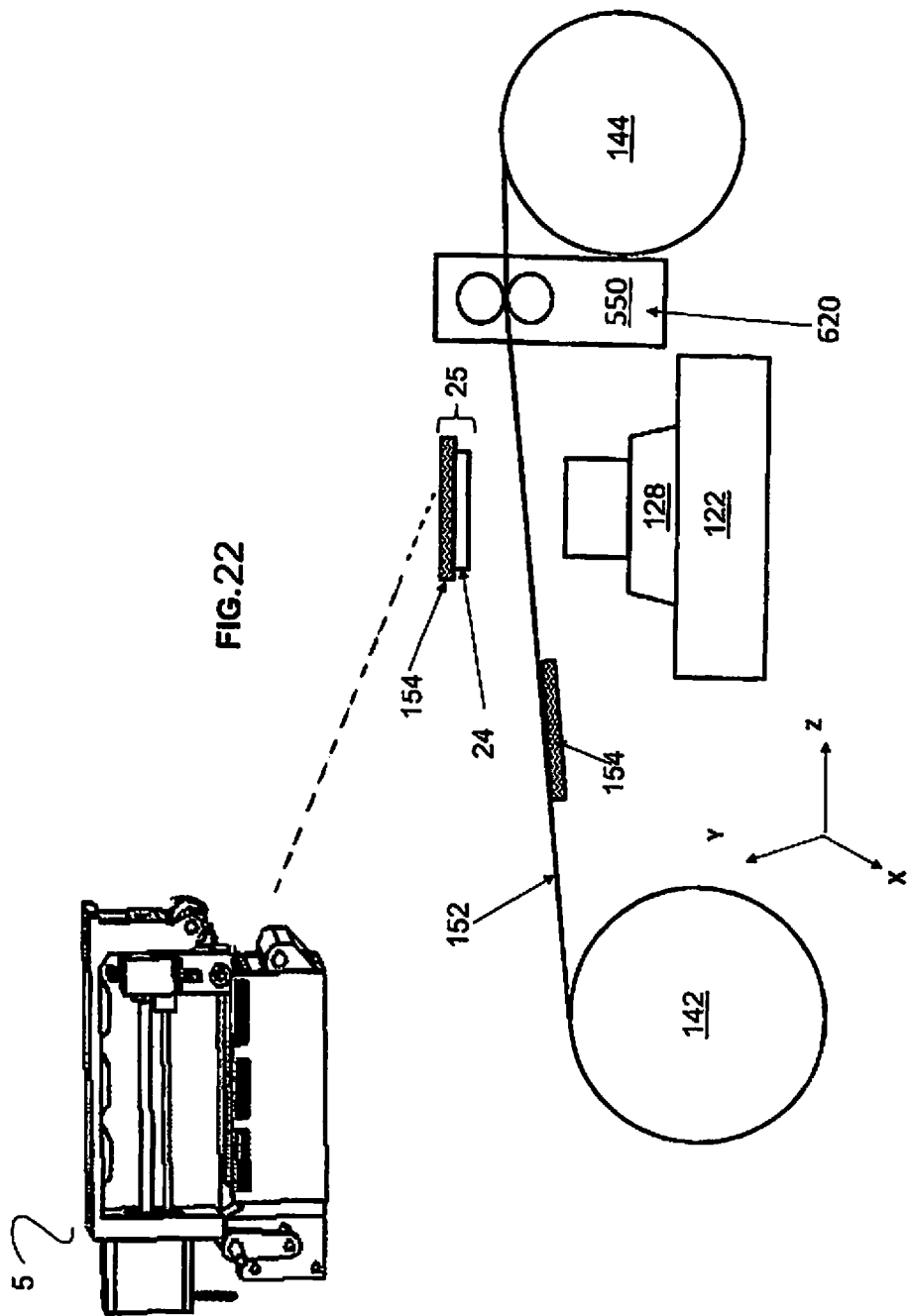

The flow charts of FIGS. 18 and 19 illustrate the steps of the motor controlled automated systems for transferring a sample to tape cut by a microtome and further transferring the sample to a slide. In the flow chart of FIG. 18, the continuous tape system of FIG. 1 is depicted; in the flow chart of FIG. 19, the discrete adhesive sections system of FIGS. 20-22 is depicted.

Turning first to FIG. 18, as shown, the feed mechanism is activated to advance the tape, i.e., a continuous length of adhesive tape. The tape is advanced from a feed mechanism such as feed mechanism 3 described above. The linear actuator member, e.g., linear actuator member 10, is moved toward the cutting face of the sample block as described above. Next, the roller, e.g., roller member 101, presses the adhesive side of the tape onto the cutting face. The roller is then pushed down to adhere the adhesive tape to cover the entire cutting face. The linear actuator is retracted to its original position to reset the roller for subsequent application of adhesive tape to another sample. The microtome then cuts the section covered by the adhesive tape (along a plane parallel or substantially parallel to the cutting face). The cut section carried by the tape is advanced to the slide station, e.g., slide station 5, to align with the slide. The slide roller presses the section on the tape onto the slide, and the section is laminated onto the slide by the various methods described above. The slide roller is retracted to its original position and the tape is advanced away from the slide, leaving the section on the slide, and stored in the take up mechanism, e.g., take up mechanism 6, described above. These steps of FIG. 18 repeat until a desired number of sample sections have been transferred to the tape, cut by the microtome and transferred to slides.

In the alternate system depicted in FIG. 19, instead of a continuous adhesive tape, discrete (spaced apart) sections of the tape are provided with adhesive and applied to the sample. More specifically, the flow chart of FIG. 19 sets forth the specific steps of the system of FIGS. 20-22.

Figure 20:
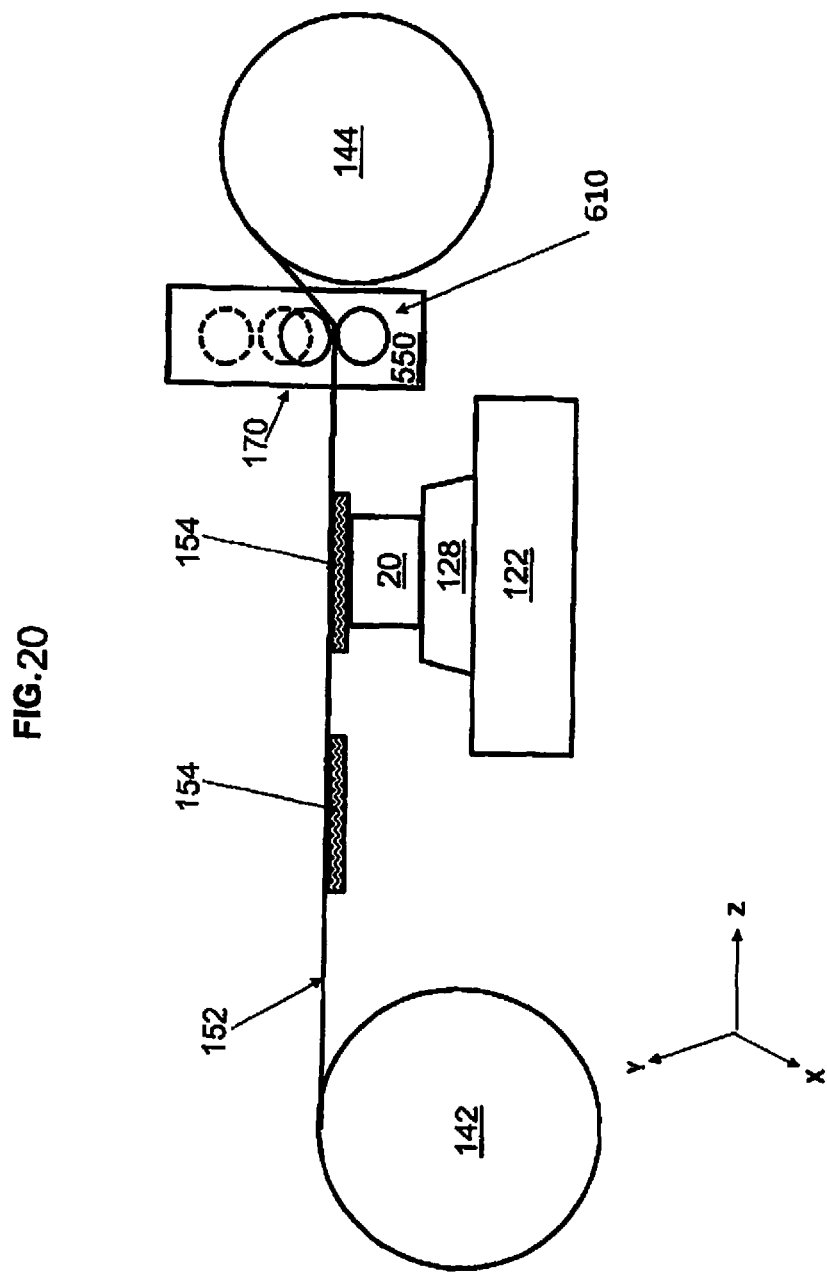
FIGS. 20-22 are partial elevated views of an alternate embodiment of the system corresponding to the system depicted in the flow chart of FIG. 19 showing the steps of transfer to the tape and movement to the slide station.

In FIG. 20, the chuck head 122 and chuck adapter 128 have advanced to a microtome-ready position, with the sample block of tissue 20 advanced to a position ready for cutting and a patch of sample tape 154, carried on the carrier strip 152 advanced from the supply spool 142, is aligned with the sample 20, i.e., disposed parallel (or substantially parallel) to and facing the surface of sample. As shown in FIG. 20, the carrier strip guide 170 is in the "Apply" position 610 so that the carrier strip 152, upon which is adhered the patch of sample tape 154, is parallel (or substantially parallel) to the surface of the sample block 20 to be cut by the microtome. The patch of sample tape 154 is applied to the surface of sample block 20 and adheres to the surface of the sample block 20, such as by an adhesive, as the carrier strip 152 is pressed onto the sample block 20.

Next, the carrier strip 152 is separated from the sample tape 154 (FIG. 21) for sectioning the sample block 20 at dotted line 23. The carrier strip guide 170 (within block 550) moves from the "Apply" position 610 of FIG. 20 to the "Remove" position 620 of FIG. 21, thus changing the angle of the carrier strip 152 relative to the sample block 20 so it is no longer parallel (or substantially parallel) to the sample block 20, and forcing the carrier strip 152 into a new path that is disposed at an angle from the sample block 20. As shown, this new path further spaces the carrier strip from the sample block 20.

Next, the sample block 20 is prepared to be sectioned. The carrier strip 152 has been separated from the sample tape 154, which is firmly adhered to the cutting face of the sample block 20, preferably covering the entire cutting face. The knife blade of the microtome makes a single cut through the sample block 20 at cut line 23 to create a specimen segment 24 (also referred to herein as a cut section) as shown in FIG. 22. Thus, FIG. 22 shows a stage of the tape application process in which the microtome operation has been completed and the specimen segment 24 is stuck to the patch of sample tape 154 (hereinafter together referred to as the tape-sample segment 25). Note the tape-sample segment 25, which includes the tape patch and cut section adhered thereto, has been removed from the knife-block and is now out of the way of the chuck head assembly. The tape sample segment 25 is then transported to the slide station 5, such as by adherence to another carrier or strip of tape (not shown) or by another converying or transport method which carries the segment 25 to the slide station for transfer to a slide in the manner described above in conjunction with the embodiments of FIGS. 1-17.

The microtome is then again ready for a microtome operation. The advancement mechanism automatically moves the chuck head 122 forward a selected amount such that the sample block (specimen) 20 is in position for the next cut of a chosen thickness. Thus, the sample block 20 is again advanced by the chuck head 122 to a microtome-ready position. The tape transport unit advances and aligns a new patch of sample tape 154 above and parallel (or substantailly parallel) to the surface of the sample block 20, and the actuator system returns the carrier strip guide 170 to the "Apply" position 610. The section is cut, removed from the carrier strip and transferred to the slide station 5. This is repeated until the desired number of samples have been cut and transferred to slides.

Note that further details of the system of FIGS. 20-22 for transferring thee sample onto the patch of sample tape are described in application Ser. No. 15/179,916, filed Jun. 10, 2016, the entire contents of which are incorporated herein by reference.

The flow chart of FIG. 19 summarizes the steps in the system of FIGS. 20-22. The feed mechanism is activated to advance the carrier strip carrying patches of sample tape with adhesive until the sample tape is aligned with the cutting face (surface) of the sample block. The roller moves to press the sample tape onto the sample surface with the carrier strip guide in the Apply position. The roller is then retracted to the initial position. The carrier strip guide moves to the Remove position to move the carrier strip out of the path and the carrier strip is separated from the sample tape. Next the microtome cuts a section of the sample. The sample tape with attached sample (tape segment) advances to the slide station, e.g., station 5 of FIG. 1, to align with a slide. The slide roller presses the sample tape onto the slide, and the sample (cut section) is laminated onto the slide by the various methods described above. The slide roller is retracted to its original position and the sample tape is removed from the cut section (sample) and slide. These steps repeat until a desired number of sample sections have been transferred to the tape, cut by the microtome and transferred to slides. Note that FIGS. 19-22 illustrate a system where the sample tape is separated from the carrier strip after being cut before transport to the slide station for transfer to slides. It is also contemplated in an alternate embodiment some of the discrete sections are maintained on the carrier strip (film) for slide transfer while other discrete sections released for direct on tape analysis or storage. Thus, in this alternate embodiment, although discrete adhesive sections are provided along the tape for individual adherence of sample tape to the sample, the sample tapes with attached sample (cut section) do not separate from the carrier strip but continue to be carried by advancement of the carrier strip into the slide station for transfer of the samples to the slides.

It should be noted that there are several other components of the slide station 5 that have not been described. For example, the slide station 5 may include an enclosure 513 (FIGS. 10 and 11) that shields the slides 5 from dust and light from the environment that can negatively affect the transfer. Likewise, the enclosure 513 also shields the operator from the UV source during operation. The interior of the enclosure 513 may be reflective to reflect UV light back towards slides for improved efficiency. The slide station 5 may also include a secondary roller 514 that is used to allow the adhesive tape 2 to travel to the take-up mechanism 6 without causing the adhesive tape 2 to become jammed or otherwise caught up in the slide station 5.

As described above, the automated tape transfer apparatus 1 may include a programmable digital controller, a processor or other type of application specific integrated circuit (ASIC) that is used to control the motion of the automated tape transfer apparatus 1, communicate with users of the automated tape transfer apparatus 1 and/or communicate with the microtome 4 to which the automated tape transfer apparatus 1 is connected. As described in detail above, there are many motions that can be controlled within the automated tape transfer apparatus 1. Examples of these motions include the movement of the feed mechanism 3 and the take-up mechanism 6, movement of the lower portion 530 and the translation portion 545 of the slide station 5, movement of the linear actuator member 103, etc. The controller may also provide information to users of the functions or conditions of the automated tape transfer apparatus 1 such as the number of slides that have been prepared, the number of sections that have been transferred, the amount of tape remaining on the roll, etc. The controller is capable of receiving any types of input (e.g., mechanical, visual, electrical, etc) to perform its control functions.

In another exemplary embodiment, the automated tape transfer apparatus 1 further includes an optical device to inspect the sample block. For example, the microtome 4 may store multiple sample blocks for sectioning. The optical device may be used to assess the condition of the cutting face or determine the location of the tissue within the embedding medium. In one example, a macro image of the cutting face may enable more precise placement of the adhesive tape 2 on the cutting face 401. Analysis of the cutting face 401 may facilitate automatic trimming of the cutting face 401 to expose the desired tissue for sectioning.

In another example, one or more optical sensors may be used to provide feedback to the controller on the position and quality of the section on the adhesive tape 2. For example, a brightness sensor in close proximity to a backlit section of the adhesive tape 2 may distinguish between an empty portion of the adhesive tape 2 and a portion that is carrying a section. This may provide an approximate location of the section on the adhesive tape 2 that may be used as an input to the controller for various purposes, such as motion control. A CCD imager or similar device may be used to image the section to provide feedback on the quality of the transfer. These images may be used to check for errors in the process, such as incomplete transfer of a section, misalignment of a section on the adhesive tape 2, presence of section trimming waste on tape, etc. In these error cases, additional sections may be taken to replace defective sections.

This visual analysis may also be employed during the block trimming process, where the microtome 4 cuts superficial or incomplete sections from the cutting face 401 to expose the sample region of interest. Visual analysis of trends in parameters such as tissue size and location during the trimming process will determine when the desired cutting face 401 is sufficiently exposed. In such cases where waste sections containing tissue are discarded, the sections may instead be acquired and stored on tape. These sections may be transferred to slides if required. A similar optical method of inspecting the section on a slide 515 may also be used. A sensor system may provide feedback of the quality of the section transfer to a slide 515 and alert the controller to errors in the process. The same or different optical sensors may be used for both tape and slide inspection.

In another exemplary embodiment, the slide station 5 may include a mechanism for the automated manipulation of slides 515. The mechanism may include a compartment for housing standard unused, clean microscope slides. When using the UV cure adhesive, slides 515 with an electrically charged surface may be prepared to promote bonding to the glass. An automatic method of dispensing and leveling adhesive onto slides may be employed. Alternatively, a mechanical arm or conveyor system may be employed to transfer slides. A conveyor, such as a conveyor belt for example, with outward facing ridges for holding slides may transfer slides to and from an unused slide storage, the slide tape applicator section (as described above with reference to FIGS. 10-12), and a section-on-slide storage location that may be included within or exterior to the housing 13 of the slide station 5. Spacing of ridges provide a method match slide spacing to section spacing on tape during section transfer.

Figure 15:
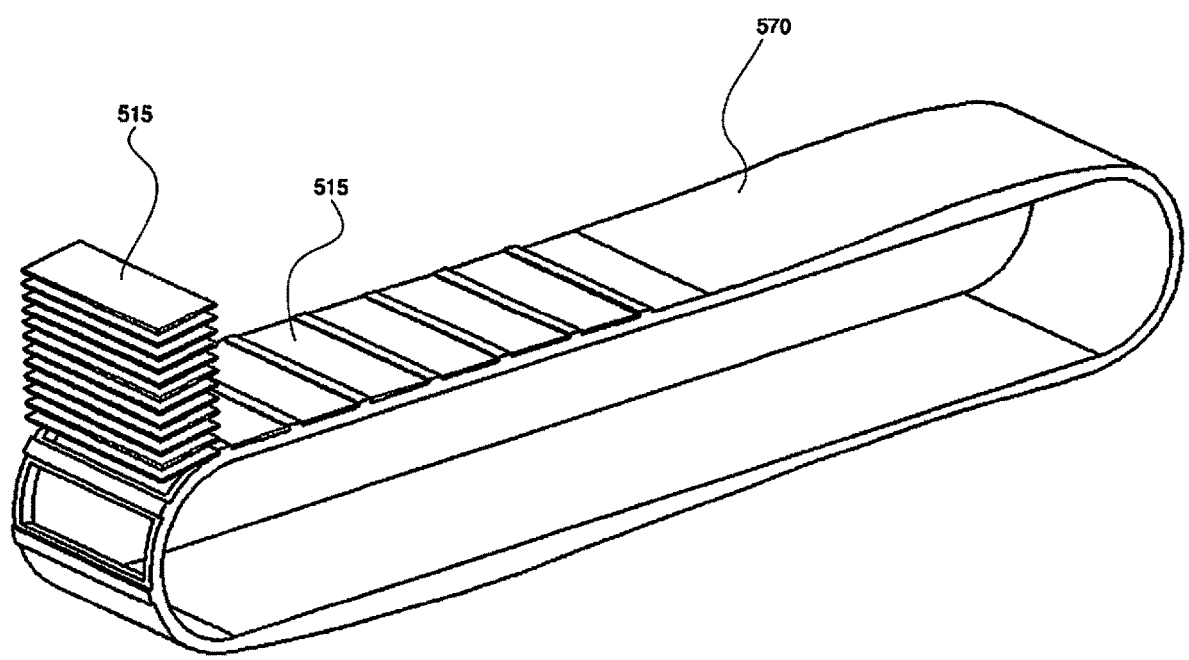
FIG. 15 shows one embodiment of a conveyor belt of the present invention for moving the slides from storage to the slide station.

FIG. 15 shows an example of a conveyor belt 570 for moving the slides 515 from storage to the slide station 5. The conveyor belt is an example of how slides can be transferred to slide station 5, it being understood that other ways to transfer the slides are also contemplated. The stack of slides 515 on the left side of FIG. 15 may be considered the slide storage. The slide storage may be included within the slide station 5 or it may be a separate component such that a portion of the conveyor belt 570 is within the slide station 5 and a portion of the conveyor belt is outside the slide station. The slides can be stored in an enclosure. The conveyor belt 570 may move the slides 515 from the storage area to the working area of the slide station 5. By allowing multiple slides to be stored within the storage area and moved automatically to the working area of the slide station, a user of the automated tape transfer apparatus 1 does not need to constantly reload the working area with new slides. The entire process of transferring the sections to the slides may then not require any user interaction, except to reload the storage area with new slides and change the adhesive tape on an occasional basis. It should also be noted that while FIG. 15 shows the loading of the new slides into the working area of the slide station 5, the conveyor belt 570 may also move the slides from the working area of the slide station 5 to another storage area for slides that have applied and adhered sections. That is, there may be a corresponding storage area at the opposite end of the conveyor belt 570 where slides having applied sections are offloaded and stored.

It should also be noted that when it is described above that the conveyor belt 570 moves the slides into the working area of the slide station 5, this does not require that the conveyor belt 570 moves directly into the area where the section and the adhesive is applied to the slide. For example, referring to the arrangement in FIG. 10, the conveyor belt 570 (not shown) may not move the slides 515 directly to the area of the support section 517. Referring to FIG. 10, the slide station 5 may also include an opening 518 through which slides 515 may move. Thus, the conveyor belt 570 may move the slides to a location near the opening 518 and a mechanism such as an arm may move the slides 515 from the conveyor belt 570 through the opening 518 to the support section 517 where the sections and adhesive is applied to the slides 515. The mechanism may then move the slides 515 back to the conveyor belt 570 for moving back to the storage area for completed slides.

It should be noted that the above is only an example and there may be other manners of moving the slides 515 from the conveyor belt 570 to the support section 517. In addition, the conveyor belt 570 may also move directly to the support section 517 such that the slides 515 do not have to be moved from the conveyor belt 570. In such an arrangement, the conveyor belt 570 may be made of a transparent material if the adhesive is a UV curable adhesive so that the UV light is able to illuminate the adhesive for the slides 515 on the conveyor belt 570. In another exemplary arrangement, mirrors or other reflectors may be used such that the UV light is guaranteed to illuminate the UV adhesive if the conveyor belt 570 is not a transparent material.

Figure 16:
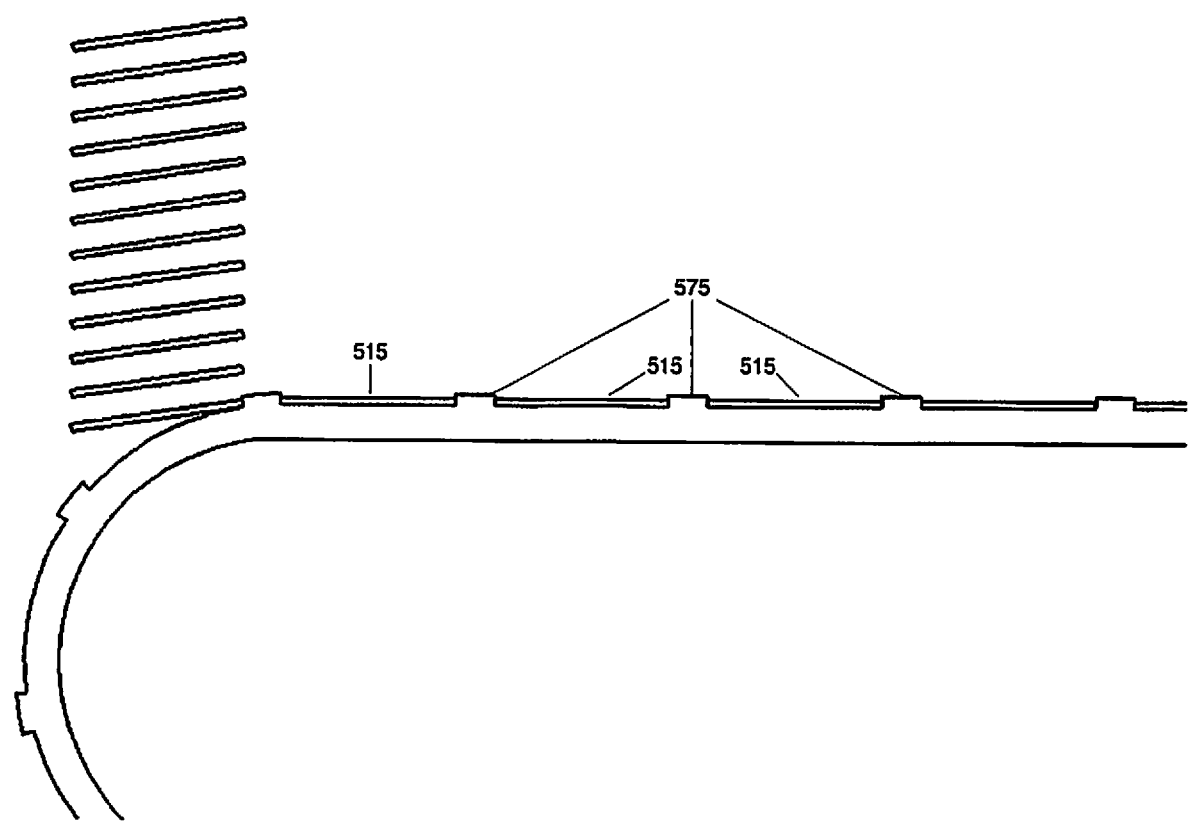
FIG. 16 shows a side view of the conveyor belt of FIG. 15.

FIG. 16 shows a further view of the exemplary conveyor belt 570. In this side view, it can be seen that the conveyor belt 570 includes a series of ridges 575 between which the slides 515 may be lodged to move the slides to the working area of the slide station 5. Specifically, the slide storage area may have a stack of slides 515 that may be gravity fed as shown in FIG. 16 (or automatically fed). As a slide 515 moves down the slide storage stack, the slide 515 may contact the conveyor belt 570 with an edge of the slide 515 contacting a ridge 575. As the conveyor belt 570 continues to move, a second edge of the slide 515 contacts the trailing ridge 575, thereby causing the slide to be lodged between the ridges 575 so that it may be moved to the working area of the slide station 5.

It should be noted that FIGS. 15 and 16 provide one example of a conveyor belt mechanism for moving the slides 515 from a storage area to a working area. The systems are not limited to such a moving mechanism. For example, other movement mechanisms may be used such as robotic arms that grasp the slides 515 and move the slides 515 from the storage area to the working area, suction type mechanisms that adhere to a portion of the slides 515 so that the slides may be moved to the working area, etc.

The automated tape transfer apparatus 1 may also include in some embodiments automated system to label slides and sample blocks with a barcode or other moniker for identification. Viable slide labeling methods include attaching an adhesive printed label, etching a label into the material or printing a label onto a dedicated location. The label may link a slide to relevant information such as the originating tissue block and sectioning date. Sample blocks may be similarly labeled. To accommodate pre-labeled blocks, an optical reader, such a barcode reader may be used to read block label to produce the relevant slide labels.

As described above, the automated tape transfer apparatus 1 may include the microtome 4 or may be a separate device that is coupled to a microtome 4. In either case, an enclosure may be provided around the microtome 4 and automated tape transfer apparatus 1 to allow for the control of ambient operating conditions such as temperature, humidity, and exposure to light.

In another embodiment, the automated tape transfer apparatus 1 may include a mechanism for automatically loading tissue sample blocks into the chuck of the microtome 4. As described above, the chuck of the microtome 4 securely holds the sample block when the microtome is sectioning the sample block. The mechanism may include a supporting platform for securing the microtome 4. The supporting platform allows for a height and distance adjustment of the microtome chuck with respect to the automated tape transfer apparatus 1 in addition to the primary methods of adjusting block height via chuck resting position and distance via tape applicator linear actuator member 3. During operation, the support platform may lock the microtome 4 position. In one example, the microtome 4 is affixed to a horizontal platform extending from the bottom of the mechanism. The platform may include a turntable allowing the microtome 4 to swivel away from automated tape transfer apparatus 1 to facilitate servicing the sample chuck and blade holder area unimpeded by the automated tape transfer apparatus 1.

In another embodiment, the automated tape transfer apparatus 1 may include an active position adjustment with respect to the position of the sample block held in the microtome 4. For example, the automated tape transfer apparatus 1 may rest upon a horizontal linear track capable of advancing or retreating the tape applicator 7 from the sample block as needed. This would facilitate consistent tape application motion regardless of sample block thickness. Furthermore, in a maximally retracted position away from the microtome 4, the tape applicator 7 may allow space to service the microtome chuck area otherwise blocked by the tape applicator 7.

Figure 17:
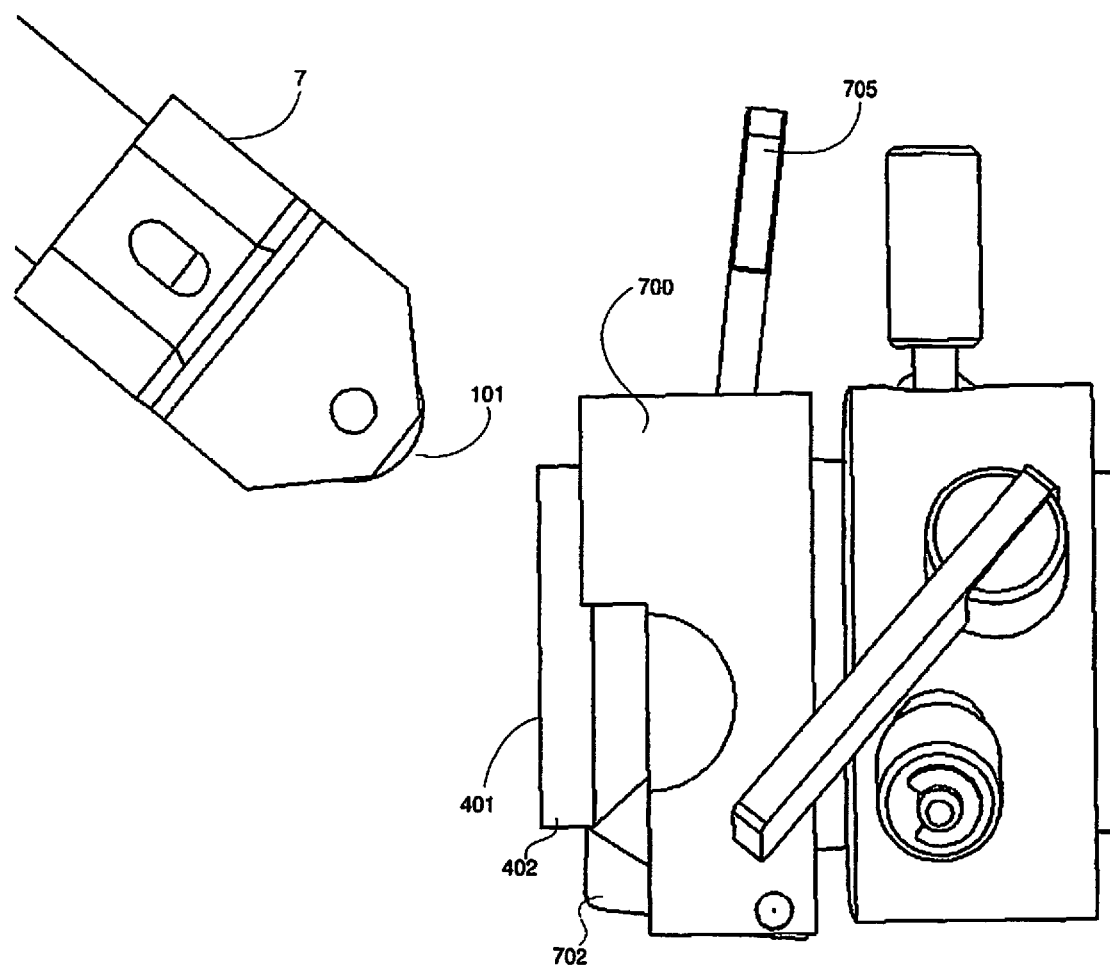
FIG. 17 shows a close-up view of the tape applicator of FIG. 1 in the region of the roller member and the cutting face.

FIG. 17 shows a close-up view of the tape applicator 7 in the region of the roller member 101 and the cutting face 401. In one exemplary operation with the tape applicator 7 in the retracted position as shown in FIG. 17, a paraffin cassette 402 may be removed from the microtome 4 chuck 700. The automated tape transfer apparatus 1 may include a system for automatically loading sample blocks into microtome chuck. While tissue cassette blocks exist in a common form factor, the chuck for holding them on the microtome naturally varies with brand and model. The exemplary automated tape transfer apparatus 1 may include a chuck 700 with a bottom clamping jaw 702 with a forward-releasing lever 705 on top seen in FIG. 17. A modular, exchangeable block loading system may allow for the automated tape transfer apparatus 1 to accommodate various microtome models. A mechanical arm may be employed to grasp the cassette without damaging the sample such as by holding the plastic base of a paraffin cassette exposed in the chuck. The mechanical arm may then engage the block release lever on top of the chuck to release it. The arm then transports the block from the microtome chuck to device block storage.

In another embodiment, the tape adhesive layer of the adhesive tape 2 is separable from the carrier film. In all the bonds that have been described above of the slide-sectiontape laminate post UV cure, e.g., between slide and section, between section and tape adhesive, and between the tape adhesive and the flexible carrier film, the bond strength between the tape adhesive and the flexible carrier film is typically the weakest bond. The bond strength between the tape adhesive and the flexible carrier film exceeds the minimum strength requirement while sectioning as described above. However, while peeling the adhesive tape 2 from the section during transfer to the slide, the tape adhesive layer may remain bonded to tissue section on the slide while the flexible carrier film is removed. That is, the tape adhesive layer remains on the slide 115 as the flexible carrier film of the adhesive tape 2 is peeled from the slide 115. The adhesive layer of the adhesive tape 2 that remains on the slide 115 may be dissolved during subsequent processing of the slide 115.

In a further embodiment, the flexible carrier film may be a reflective material such as metalized Mylar. During the UV curing process, the flexible carrier film reflects light back through the UV adhesive towards the UV source 119 for more efficient UV curing. The UV adhesive may not absorb 100% of the UV light. Reflecting the UV light gives the UV adhesive another chance to absorb the UV light to catalyze the adhesive cure. In a further embodiment, a solvent applied to the slide-section-tape laminate may weaken the tape adhesive prior to peeling the adhesive tape 2 off of the section.

In implementations where an adhesive tape 2 with a UV release adhesive is used, an alternate tape-to-slide transfer process may be used. For example, due to the decrease in the adhesive strength of the adhesive tape 2 after UV irradiation, the UV-curable slide adhesive may be substituted with a weaker adhesive solution not requiring the UV cure process. The viscosity and adhesion between the slide, non-UV adhesive solution, and section should be sufficient to retain the section on the slide when peeling the adhesive tape. Subsequently, the section may expand on the slide solution akin to the water bath in the traditional process. The slide may be heated to aid in section expansion. Finally, excess solution may be removed such as by evaporation to affix the section to slide.

In another embodiment, the tape adhesive layer may exhibit viscoelastic characteristics allowing sections on the adhesive tape 2 to expand. In the "traditional" manual sectioning process, expanding the tissue sections is accomplished via floating the sections on warm water. Section expansion is desirable to restore tissue from tissue compression caused during the prior embedding process for creating sample blocks. The adhesive tape 2 will still function in supporting the section during the cutting process because the cut occurs quickly enough such that the adhesive response is functionally elastic. On the other hand, the expansion of section on tape occurs slowly enough such that the adhesive response is primarily viscous. Heat may then be applied to the section on adhesive tape 2 to facilitate thermal expansion of tissue section.

In another embodiment, the adhesive tape 2 may include an additional release layer between the tape adhesive layer and the flexible carrier film. The release layer may be a thermoplastic layer, which, when melted, has the additional advantage of allowing sections to expand on tape. Bond strength between the adhesive layer and the carrier layers (e.g., the additional release layer and the flexible carrier film) may then be weakened in lieu of weakening the bond between the adhesive layer of the adhesive tape 2 and the section prior to peeling the adhesive tape 2 off of the section cured to the slide via modifying this release layer. The aforementioned methods of solvents, heating, cooling, or UV radiation may be used to weaken the additional release layer.

In another embodiment, not all the sections that have been adhered to the adhesive tape 2 are transferred to the slides 115. For example, the adhesive tape 2 may advance through the slide station 5 without transferring the sections to the slides 115. This may occur because the user of the slides may not need to see every section that has been sectioned from the section block. However, the user may desire to go back and look at these sections at a later time. Thus, in this exemplary embodiment, the adhesive tape 2 that still includes some sections that have not been transferred to slides 115 may be taken up on a take-up reel that is coupled to the take-up mechanism 6. The take-up reel may then be stored (e.g., in frozen storage or cooled storage) so that the sections that are adhered to the adhesive tape 2, but not transferred to slides 115 may be transferred at a later date. The take-up reels may be labeled as described above with section identifiers and/or sample block identifiers such that the correct take-up reels may be later retrieved.

It will be apparent to those skilled in the art that various modifications may be made in the present invention, without departing from the spirit or scope of the invention. Thus, it is intended that the present invention cover the modifications and variations of this invention provided they come within the scope of the appended claims and their equivalents.

What is claimed is:

1. An automated method for advancing a tape comprising the following automated controller controlled steps:
    pressing a first portion of a continuous length of an adhesive tape to a first cutting face of a sample block so the adhesive tape contacts and adheres to and covers the first cutting face;
    after adherence of the tape to the first cutting face, cutting a first section from the sample block;
    moving the first portion of the adhesive tape away from the sample block after the first section has been cut from the sample block, wherein the first section is adhered to the first portion of the adhesive tape and the cutting exposes a second cutting face of the sample block;
    pressing a second portion of the adhesive tape to the second cutting face of the sample block;
    after adherence of the tape to the second cutting face and covering of the second cutting face, cutting a second section from the sample block;
    moving the second portion of the adhesive tape away from the sample block after a second section has been cut from the sample block, wherein the second section is adhered to the second portion of the adhesive tape;
    moving the first and second portions of the adhesive tape carrying the corresponding first and second sections to a slide station, the slide station supporting at least first and second slides; and
    pressing the first section to the first slide in the slide station to transfer the first section to the first slide and pressing the second section to the second slide in the slide station to transfer the second section to the second slide, wherein the step of pressing the first section includes moving a roller or a cam within a slide station to press the first section on the first slide, the slide movable in an axial direction and the roller movable from a first position axially spaced from the first slide to a second position over the first slide to press the first section on the first slide; and wherein the foregoing steps are all performed by an automated controller controlled apparatus.

2. The method of claim 1, wherein the first and second slides are moved along a conveyor to a position to enable sequential transfer of the first section to the first slide and the second section to the second slide in the slide station.

3. The method of claim 1, further comprising the step of controlling a distance between the first portion and second portion of the adhesive tape.

4. The method of claim 1, further comprising the step of controlling one or more of a speed, acceleration and jerk of moving operations.

5. The method of claim 1, wherein the step of pressing the first portion of the adhesive tape to the first cutting face includes pressing the roller member or the cam that holds the adhesive tape in a direction against the cutting face throughout an entire length of the cutting face.

6. The method of claim 1, wherein the step of pressing the first portion of the adhesive tape fully covers the first cutting face with an adhesive region of the adhesive tape prior to the step of cutting the first section.

7. The method of claim 1, wherein the sample block comprises a tissue sample enclosed in a supporting block of paraffin.

8. The method of claim 1, further comprising the step of heating, cooling or applying UV light to the tape to change the properties of the tape to lower an adhesive strength of the tape subsequent to the step of transferring the first section to the first slide and prior to a step of removing the tape from the first section on the slide.

9. The method of claim 1, further comprising a take-up mechanism that takes up the adhesive tape after the adhesive tape has exited the slide station.

10. The method of claim 1, further comprising the step of pre-coating with a UV-curable adhesive the first and second slides in the slide station.

11. The method of claim 1, wherein the method further comprises the step of applying UV-curable adhesive and activating the adhesive by applying a UV light source positioned below the slides.

12. The method of claim 1, further comprising the step of imaging the sample block via an optical device during the automated method to assess a condition of the cutting of the sample block.

13. The method of claim 1, further comprising the step of providing one or more optical sensors or imaging devices to provide feedback on a position and a quality of the first section and second section on the adhesive tape.

14. The method of claim 1, wherein the slide station contains a plurality of slides arranged in an array.

15. The method of claim 9, wherein the slide station contains a plurality of slides arranged in an array and the take up mechanism is downstream of the slide station.

16. An automated method for advancing a tape comprising the following automated controller controlled steps:
pressing a first portion of a continuous length of an adhesive tape to a first cutting face of a sample block so the adhesive tape contacts and adheres to and covers the first cutting face;
after adherence of the tape to the first cutting face, cutting a first section from the sample block;
moving the first portion of the adhesive tape away from the sample block after the first section has been cut from the sample block, wherein the first section is adhered to the first portion of the adhesive tape and the cutting exposes a second cutting face of the sample block;
pressing a second portion of the adhesive tape to the second cutting face of the sample block;
after adherence of the tape to the second cutting face and covering of the second cutting face, cutting a second section from the sample block;
moving the second portion of the adhesive tape away from the sample block after a second section has been cut from the sample block, wherein the second section is adhered to the second portion of the adhesive tape;
moving the first and second portions of the adhesive tape carrying the corresponding first and second sections to a slide station, the slide station supporting at least first and second slides;
pressing the first section to the first slide in the slide station to transfer the first section to the first slide and pressing the second section to the second slide in the slide station to transfer the second section to the second slide;
wherein the foregoing steps are all performed by an automated controller controlled apparatus and
indicating via an optical device during the automated method that the tape has been adhered to the cutting face prior to the step of cutting the first section from the sample block wherein the first section is cut by a microtome.

17. An automated method for advancing a tape comprising the following automated controller controlled steps:
pressing a first portion of a continuous length of an adhesive tape to a first cutting face of a sample block so the adhesive tape contacts and adheres to and covers the first cutting face;
after adherence of the tape to the first cutting face, cutting a first section from the sample block:
moving the first portion of the adhesive tape away from the sample block after the first section has been cut from the sample block, wherein the first section is adhered to the first portion of the adhesive tape and the cutting exposes a second cutting face of the sample block;
pressing a second portion of the adhesive tape to the second cutting face of the sample block:
after adherence of the tape to the second cutting face and covering of the second cutting face, cutting a second section from the sample block;
moving the second portion of the adhesive tape away from the sample block after a second section has been cut from the sample block, wherein the second section is adhered to the second portion of the adhesive tape;
moving the first and second portions of the adhesive tape carrying the corresponding first and second sections to a slide station, the slide station supporting at least first and second slides; and
pressing the first section to the first slide in the slide station to transfer the first section to the first slide and pressing the second section to the second slide in the slide station to transfer the second section to the second slide, wherein the step of pressing the first section includes moving a roller within the slide station to press the first section on the first slide, the roller movable by linear movement of a translation portion of the slide station to release the first section from the tape, the roller moving substantially parallel to a longitudinal axis of the slide;
wherein the foregoing steps are all performed by an automated controller controlled apparatus.

18. The method of claim 17, wherein the step of moving the roller moves the roller linearly parallel to an upper surface of the slide and the roller applies a constant force on the adhesive tape during application of the first section to the first slide.

* * * * *